(12) United States Patent
Vitt et al.

(10) Patent No.: US 8,354,433 B2
(45) Date of Patent: Jan. 15, 2013

(54) ANTI-INFLAMMATORY AGENTS AS VIROSTATIC COMPOUNDS

(75) Inventors: Daniel Vitt, Germering (DE); Manfred Groeppel, Stockdorf (DE); Roland Baumgartner, Planegg-Martinsried (DE); Johann Leban, Planegg-Martinsried (DE)

(73) Assignee: 4SC AG, Planegg-Martinsried (DE)

( * ) Notice: Subject to any disclaimer, the term of this patent is extended or adjusted under 35 U.S.C. 154(b) by 247 days.

(21) Appl. No.: 12/772,470

(22) Filed: May 3, 2010

(65) Prior Publication Data

US 2010/0280081 A1 Nov. 4, 2010

Related U.S. Application Data

(60) Provisional application No. 61/175,255, filed on May 4, 2009.

(30) Foreign Application Priority Data

May 4, 2009 (EP) .................................... 09159358

(51) Int. Cl.
*A61K 31/44* (2006.01)
(52) U.S. Cl. ...................................................... 514/332
(58) Field of Classification Search ................. 514/332; 546/262
See application file for complete search history.

(56) References Cited

FOREIGN PATENT DOCUMENTS

| WO | WO/03/006425 | * | 1/2003 |
|---|---|---|---|
| WO | WO/2004/056746 | * | 7/2004 |
| WO | WO/2004/056747 | * | 7/2004 |
| WO | WO/2004/056797 | * | 7/2004 |
| WO | WO-2008 077639 | | 7/2008 |
| WO | WO-2009 021696 | | 2/2009 |

* cited by examiner

*Primary Examiner* — Taofiq A Solola
(74) *Attorney, Agent, or Firm* — Millen, White, Zelano & Branigan, P.C.

(57) ABSTRACT

The present invention relates to compounds of the general formula (I) and salts and physiologically functional derivatives thereof,

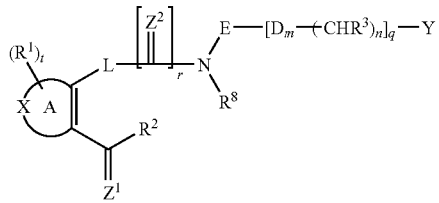

for the use as a medicament.

24 Claims, 1 Drawing Sheet

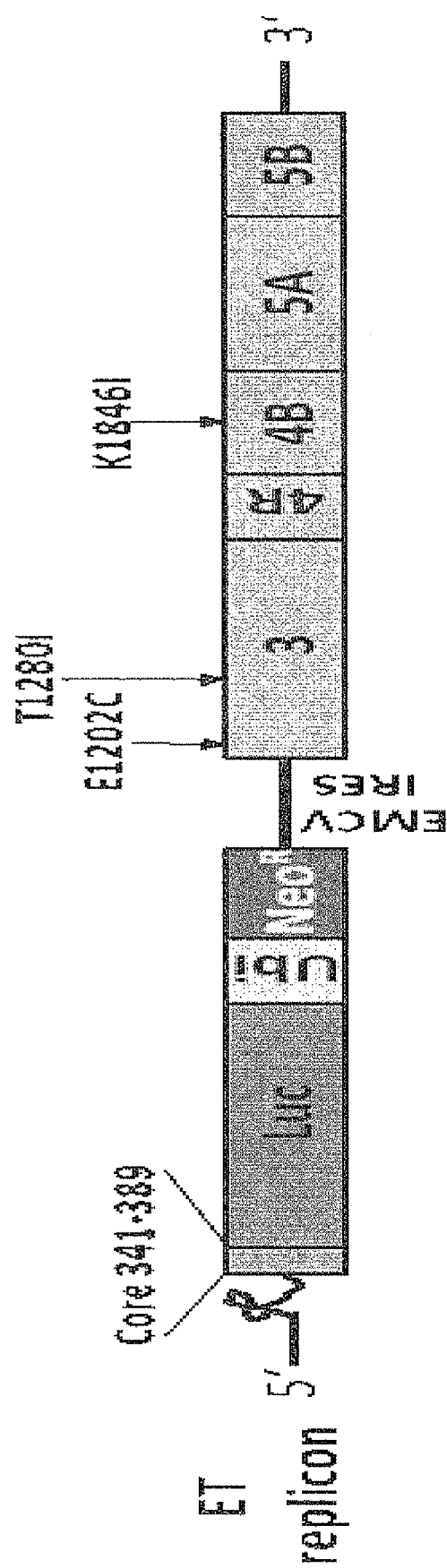

ANTI-INFLAMMATORY AGENTS AS VIROSTATIC COMPOUNDS

This application claims the benefit of the filing date of U.S. Provisional Application Ser. No. 61/175,255 filed May 4, 2009.

The present invention relates to compounds that have been described as anti-inflammatory, immunomodulatory and antiproliferatory agents and surprisingly show virostatic activities. In particular the invention refers to the use of compounds which inhibit dihydroorotate dehydrogenase (DHODH), for the treatment and prevention of viral diseases, in particular HCMV, HIV, HCV, HBV, and influenza.

Viral infections are usually treated with substances targeting viral proteins, e.g. influenza is treated with M2-membrane protein inhibitors (adamantin and rimantadin) or neuraminidase inhibitors (oseltamivir and zanamivir); HIV is treated with HIV protease inhibitors, reverse transcriptase inhibitors (nucleoside and non-nucleoside analoga), fusion inhibitors (blocking the viral transmembrane protein gp41) or cell entry inhibitors; HCV is treated by a combination of ribavirin and interferone alpha, where ribavirin as a nucleoside analogue inhibits the viral polymerase, and interferone alpha activates the host immune system; HBV is treated with pegylated interferone alpha and/or nucleoside or nucleotide analoga.

However, treatment of these viral diseases is not satisfactory due to the high mutation rate of viruses and the thus resulting lack of efficacy of presently known medications. Moreover, severe side effects caused by interaction with host factors or by incompatibility of treatments for patients who are infected with two or several different viruses occur regularly. In view of the viruses' abilities to quickly adapt to new selection pressures caused by substances targeting viral proteins, new treatment options for viral diseases are urgently required. A new approach to circumvent the selection pressure on viruses and thus avoid the generation of resistances is the targeting of host cell factors vital for the viral replication cycle.

The active metabolite of leflunomide, a DHODH inhibitor with a completely different structure has been discussed and tested lately in several viral infection models as well as in infected patients (Gabriel T. Meister, dissertation Ohio State University 2005; Chong et al. Am. J. Transplant 2006 6(1): 69-75), however, anti-viral activity is largely attributed to the inhibition of protein kinases which results in inhibition of phosphorylation of viral proteins. Moreover, administration of uridine in viral plaque assays did not affect the reduction of viral loads in a cytomegalovirus (CMV) model; an inhibitor exerting its activity by the inhibition of DHODH, however, according to the above-cited publications would be expected to lose its inhibitory potential when the assay is supplemented with uridine.

The compounds to which this invention relates have been described as DHODH inhibitors before (WO 03/006425, WO 04/056746, WO 04/056797, WO04056747, WO 08/077639, WO 09/021696), and the treatment of diseases caused by viral infections has been mentioned.

The pathogenity of viruses heavily relies on host cell machinery for replication, leading to a high need of nucleobase building blocks due to the high replication rate of the viruses. It has now been found unexpectedly, that the inhibition of DHODH, which leads to an inhibition of the de novo biosyntheses of pyrimidines can be exploited to suppress the replication of certain viruses.

Here we disclose that the use of substances according to formula I is particularly advantageous for the treatment of diseases caused by the following viruses:

Human Immunodeficiency Virus (HIV), Hepatitis C Virus (HCV), Hepatitis B Virus (HBV), and Influenza. BK-Polyomavirus (BKV) Human Cytomegaly Virus (HCMV), Rift Valley Fever Virus (RVFV), Norovirus (NV), Lassa Virus (LV), Ebolavirus (EBOV), West Nile Virus (WNV), Dengue Virus (DV), Yellow fever virus (YFV), Human Respiratory Syncytial Virus (RSV).

Thus, in particular, the subject of the present invention comprises the following aspects:

1. A dihydroorotate-dehydrogenase inhibitor for use in the treatment or amelioration of a disease or medical condition caused by a viral infection by double stranded DNA viruses (dsDNA viruses), positive-sense single-stranded RNA viruses ((+)ssRNA viruses), negative-sense single-stranded RNA viruses ((−)ssRNA viruses), double-stranded DNA viruses (dsDNA), single-stranded RNA viruses which use a DNA intermediate to replicate (ss-RNA-RT viruses), double-stranded DNA viruses which use an RNA intermediate during genome replication (ds-DNA-RT viruses), wherein the dihydroorotate-dehydrogenase inhibitor is not leflunomide or a metabolite thereof.

2. A dihydroorotate-dehydrogenase inhibitor according to aspect 1 for use in the treatment or amelioration of a disease or medical condition caused by a viral infection by a virus selected from the group comprising Human Immunodeficiency Virus (HIV), Hepatitis C Virus (HCV), Hepatitis B Virus (HBV), and Influenza, BK-Polyomavirus (BKV), Human Cytomegaly Virus (HCMV), Rift Valley Fever *Virus (RVFV), Norovirus (NV), Lassa Virus (LV), Ebolavirus (EBOV), West Nile Virus (WNV), Dengue Virus (DV), Human Respiratory Syncytial Virus (RSV), Yellow fever virus (YFV).

3. A dihydroorotate-dehydrogenase inhibitor for use in the treatment or amelioration of a disease or medical condition caused by a viral infection according to aspect 1 or 2, wherein the dihydroorotate-dehydrogenase inhibitor has a half-maximal inhibitory concentration ($IC_{50}$) of 50 nM or less for the inhibition of dihydroorotate-dehydrogenase or less in an in vitro assay and a half-maximal effective concentration ($EC_{50}$) of 200 nM or less for inhibition of viruses in an in vitro assay.

4. A dihydroorotate-dehydrogenase inhibitor for use in the treatment or amelioration of a disease or medical condition caused by a viral infection according to any of aspects 1 to 3, wherein the dihydroorotate-dehydrogenase inhibitor has a solubility in water of 10 µg/mL or greater and/or an absolute oral availability (F) of 30% or greater.

5. A dihydroorotate-dehydrogenase inhibitor for use in the treatment or amelioration of a disease or medical condition caused by a viral infection according to any of aspects 1 to 4, wherein the dihydroorotate-dehydrogenase inhibitor is a compound of the general formula (I) or a physiologically functional derivative or a pharmacologically tolerable salt thereof, (Formula I)

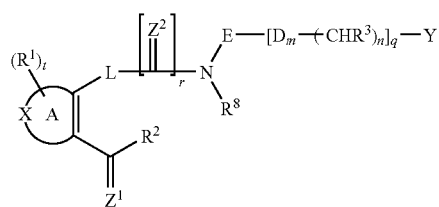

wherein

A is an aromatic or non-aromatic 5- or 6-membered hydrocarbon ring wherein optionally one or more of the carbon atoms are replaced by a group X, wherein X is independently selected from the group consisting of S, O, N, $NR^4$, $SO_2$ and SO;

L is a single bond or NH

D is O, S, $SO_2$, $NR^4$, or $CH_2$;

$Z^1$ is O, S, or $NR^5$;

$Z^2$ is O, S, or $NR^5$;

$R^1$ independently represents H, halogen, haloalkanyl, haloalkenyl, haloalkynyl, haloalkanyloxy, haloalkenyloxy, haloalkynyloxy, —$CO_2R''$, —$SO_3H$, —OH, —CONR*R'', —CR''O, —$SO_2$—NR*R'', —$NO_2$, —$SO_2$—R'', —SO—R*, —CN, alkanyloxy, alkenyloxy, alkynyloxy, alkanylthio, alkanylthio, alkynylthio, aryl, —NR''—$CO_2$—R', —NR''—CO—R*, —NR''—$SO_2$—R', —O—CO—R*, —O—$CO_2$—R*, —O—CO—NR*R''; cycloalkyl, heterocycloalkyl, alkanylamino, alkenylamino, alkynylamino, hydroxyalkanylamino, hydroxyalkenylamino, hydroxyalkynylamino, —SH, heteroaryl, alkanyl, alkenyl or alkynyl;

R* independently represents H, alkanyl, alkenyl, alkynyl, cycloalkyl, heterocycloalkyl, aminoalkanyl, aminoalkenyl, aminoalkynyl, alkanyloxy, alkenyloxy, alkynyloxy, —OH, —SH, alkanylthio, alkenylthio, alkynylthio, hydroxyalkanyl, hydroxyalkenyl, hydroxyalkynyl, haloalkanyl, haloalkenyl, haloalkynyl, haloalkanyloxy, haloalkenyloxy, haloalkynyloxy, aryl or heteroaryl;

R' independently represents H, —$CO_2R''$, —CONR''R''', —CR''O, —$SO_2NR''$, —NR''—CO-haloalkanyl, haloalkenyl, haloalkynyl, —$NO_2$, —NR''—$SO_2$-haloalkanyl, haloalkenyl, haloalkynyl, —NR''—$SO_2$-alkanyl, —NR''—$SO_2$-alkenyl, —NR''—$SO_2$-alkynyl, —$SO_2$-alkanyl, —$SO_2$-alkenyl, —$SO_2$-alkynyl, —NR''—CO-alkanyl, —NR''—CO-alkenyl, —NR''—CO-alkynyl, —CN, alkanyl, alkenyl, alkynyl, cycloalkyl, heterocycloalkyl, aminoalkanyl, aminoalkenyl, aminoalkynyl, alkanylamino, alkenylamino, alkynylamino, alkanyloxy, alkenyloxy, alkynyloxy, cycloalkyloxy, —OH, —SH, alkanylthio, alkenylthio, alkynylthio, hydroxyalkanyl, hydroxyalkenyl, hydroxyalkynyl, hydroxyalkanylamino, hydroxyalkenylamino, hydroxyalkynylamino, halogen, haloalkanyl, haloalkenyl, haloalkynyl, haloalkanyloxy, haloalkenyloxy, haloalkynyloxy, aryl, aralkyl or heteroaryl;

R'' independently represents hydrogen, haloalkanyl, haloalkenyl, haloalkynyl, hydroxyalkanyl, hydroxyalkenyl, hydroxyalkynyl, alkanyl, alkenyl, alkynyl, cycloalkyl, heterocycloalkyl, aryl, heteroaryl, aminoalkanyl, aminoalkenyl or aminoalkynyl R''' independently represents H or alkanyl $R^2$ is H or $OR^6$, $NHR^7$, $NR^7OR^7$;
  or $R^2$ together with the nitrogen atom which is attached to $R^8$ forms a 5 to 7 membered, preferably 5 or 6 membered heteroyclic ring wherein $R^2$ is —$[CH_2]_s$ and $R^8$ is absent;

$R^3$ is H, alkanyl, alkenyl, alkynyl, cycloalkyl, heterocycloalkyl, aryl, alkanyloxy, alkenyloxy, alkynyloxy, —O-aryl; —O-cycloalkyl, —O-heterocycloalkyl, halogen, aminoalkanyl, aminoalkenyl, aminoalkynyl, alkanylamino, alkenylamino, alkynylamino, hydroxylamino, hydroxylalkanyl, hydroxylalkenyl, hydroxylalkynyl, haloalkanyloxy, haloalkenyloxy, haloalkynyloxy, heteroaryl, alkanylthio, alkenylthio, alkynylthio, —S-aryl; —S-cycloalkyl, —S-heterocycloalkyl, aralkyl, haloalkanyl, haloalkenyl or haloalkynyl;

$R^4$ is H, alkanyl, alkenyl, alkynyl, cycloalkyl, heterocycloalkyl, aryl or heteroaryl;

$R^5$ is H, OH, alkanyloxy, alkenyloxy, alkynyloxy, O-aryl, alkanyl, alkenyl, alkynyl or aryl;

$R^6$ is H, alkanyl, alkenyl, alkynyl, cycloalkyl, heterocycloalkyl, aryl, heteroaryl, aralkyl, alkanyloxyalkanyl, alkanyloxyalkenyl, alkanyloxyalkynyl, alkenyloxyalkanyl, alkenyloxyalkenyl, alkenyloxyalkynyl, alkynyloxyalkanyl, alkynyloxyalkenyl, alkynyloxyalkynyl, acylalkanyl, (acyloxy)alkanyl, (acyloxy)alkenyl, (acyloxy)alkynyl acyl, non-symmetrical (acyloxy)alkanyldiester, non-symmetrical (acyloxy)alkenyldiester, non-symmetrical (acyloxy)alkynyldiester, or dialkanylphosphate, dialkenylphosphate or dialkynylphosphate;

$R^7$ is H, OH, alkanyl, alkenyl, alkynyl, aryl, alkanyloxy, alkenyloxy, alkynyloxy, —O-aryl, cycloalkyl, heterocycloalkyl, or —O-cycloalkyl, —O-heterocycloalkyl;

$R^8$ is hydrogen, alkanyl, alkenyl or alkynyl;

E is an alkanyl, alkenyl, alkynyl, aryl, heteroaryl, heterocycloalkyl or cycloalkyl group or a fused bi- or tricyclic ring system wherein one phenyl ring is fused to one or two monocyclic cycloalkyl or heterocycloalkyl rings or one bicyclic cycloalkyl or heterocycloalkyl ring, or wherein two phenyl rings are fused to a monocyclic cycloalkyl or heterocycloalkyl ring, wherein monocyclic and bicyclic cycloalkyl and heterocycloalkyl rings are as defined herein, and wherein all of the aforementioned groups may optionally be substituted by one or more substituents R'

Y is hydrogen, halogen, haloalkenyl, haloalkenyl, haloalkynyl, haloalkanyloxy, haloalkenyloxy, haloalkynyloxy, alkanyl, alkenyl, alkynyl, aryl, heteroaryl, heterocycloalkyl or cycloalkyl group or a fused bi- or tricyclic ring system wherein one phenyl ring is fused to one or two monocyclic cycloalkyl or heterocycloalkyl rings or one bicyclic cycloalkyl or heterocycloalkyl ring, or wherein two phenyl rings are fused to a monocyclic cycloalkyl or heterocycloalkyl ring, and wherein all of the aforementioned groups may optionally be substituted by one or more substituents R', or Y is

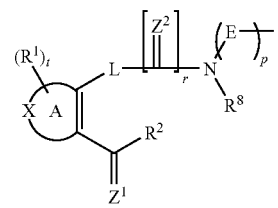

wherein $R^1$, X, A, $Z^1$, $Z^2$, $R^8$, $R^2$, E and p are as defined herein;

m is 0 or 1;
n is 0 or 1;
p is 0 or 1;
q is 0 or 1;
r is 0 or 1;
s is 0 to 2; and
t is 0 to 3.

6. A pharmaceutical composition comprising a compound as defined in any of aspects 1 to 5 in free form or in the form of a pharmaceutically acceptable salt or physiologically functional derivative and a pharmaceutically acceptable diluent or carrier for use in the treatment or amelioration of a disease or medical condition caused by a viral infection.

7. A compound according to any of aspects 1 to 5 or a composition according to aspect 6 wherein the disease or indication is selected from the group comprising transplant rejection.

Compounds of Formula (I) comprise the following substances:

Formula I:

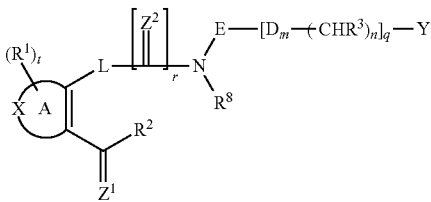

wherein

A is an aromatic or non-aromatic 5- or 6-membered hydrocarbon ring wherein optionally one or more of the carbon atoms are replaced by a group X, wherein X is independently selected from the group consisting of S, O, N, $NR^4$, $SO_2$ and SO;

L is a single bond or NH

D is O, S, $SO_2$, $NR^4$, or $CH_2$;

$Z^1$ is O, S, or $NR^5$, $Z^2$ is O, S, or $NR^5$;

$R^1$ independently represents H, halogen, haloalkanyl, haloalkenyl, haloalkynyl, haloalkanyloxy, haloalkenyloxy, haloalkynyloxy, —$CO_2R"$, —$SO_3H$, —OH, —$CONR*R"$, —CR"O, —$SO_2$—NR*R", —$NO_2$, —$SO_2$—R", —SO—R*, —CN, alkanyloxy, alkenyloxy, alkynyloxy, alkanylthio, alkenylthio, alkynylthio, aryl, —NR"—$CO_2$—R', —NR"—CO—R*, —NR"—$SO_2$—R', —O—CO—R*, —O—$CO_2$—R*, —O—CO—NR*R"; cycloalkyl, heterocycloalkyl, alkanylamino, alkenylamino, alkynylamino, hydroxyalkanylamino, hydroxyalkenylamino, hydroxyalkynylamino, —SH, heteroaryl, alkanyl, alkenyl or alkynyl;

R* independently represents H, alkanyl, alkenyl, alkynyl, cycloalkyl, heterocycloalkyl, aminoalkanyl, aminoalkenyl, aminoalkynyl, alkanyloxy, alkenyloxy, alkynyloxy, —OH, —SH, alkanylthio, alkenylthio, alkynylthio, hydroxyalkanyl, hydroxyalkenyl, hydroxyalkynyl, haloalkanyl, haloalkenyl, haloalkynyl, haloalkanyloxy, haloalkenyloxy, haloalkynyloxy, aryl or heteroaryl;

R' independently represents H, —$CO_2R"$, —$CONR"R'"$, —CR"O, —$SO_2NR"$, —NR"—CO-haloalkanyl, haloalkenyl, haloalkynyl, —$NO_2$, —NR"—$SO_2$-haloalkanyl, haloalkenyl, haloalkynyl, —NR"—$SO_2$-alkanyl, —NR"—$SO_2$-alkenyl, —NR"—$SO_2$-alkynyl, —$SO_2$-alkanyl, —$SO_2$-alkenyl, —$SO_2$-alkynyl, —NR"—CO-alkanyl, —NR"—CO-alkenyl, —NR"—CO-alkynyl, —CN, alkanyl, alkenyl, alkynyl, cycloalkyl, heterocycloalkyl, aminoalkanyl, aminoalkenyl, aminoalkynyl, alkanylamino, alkenylamino, alkynylamino, alkanyloxy, alkenyloxy, alkynyloxy, -cycloalkyloxy, —OH, —SH, alkanylthio, alkenylthio, alkynylthio, hydroxyalkanyl, hydroxyalkenyl, hydroxyalkynyl, hydroxyalkanylamino, hydroxyalkenylamino, hydroxyalkynylamino, halogen, haloalkanyl, haloalkenyl, haloalkynyl, haloalkanyloxy, haloalkenyloxy, haloalkynyloxy, aryl, aralkyl or heteroaryl;

R" independently represents hydrogen, haloalkanyl, haloalkenyl, haloalkynyl, hydroxyalkanyl, hydroxyalkenyl, hydroxyalkynyl, alkanyl, alkenyl, alkynyl, cycloalkyl, heterocycloalkyl, aryl, heteroaryl, aminoalkanyl, aminoalkenyl or aminoalkynyl R'" independently represents H or alkanyl $R^2$ is H or $OR^6$, $NHR^7$, $NR^7OR^7$;

or $R^2$ together with the nitrogen atom which is attached to $R^8$ forms a 5 to 7 membered, preferably 5 or 6 membered heteroyclic ring wherein $R^2$ is —[$CH_2$], and $R^8$ is absent;

$R^3$ is H, alkanyl, alkenyl, alkynyl, cycloalkyl, heterocycloalkyl, aryl, alkanyloxy, alkenyloxy, alkynyloxy, —O-aryl; —O-cycloalkyl, —O-heterocycloalkyl, halogen, aminoalkanyl, aminoalkenyl, aminoalkynyl, alkanylamino, alkenylamino, alkynylamino, hydroxylamino, hydroxylalkanyl, hydroxylalkenyl, hydroxylalkynyl, haloalkanyloxy, haloalkenyloxy, haloalkynyloxy, heteroaryl, alkanylthio, alkenylthio, alkynylthio, —S-aryl; —S-cycloalkyl, —S-heterocycloalkyl, aralkyl, haloalkanyl, haloalkenyl or haloalkynyl;

$R^4$ is H, alkanyl, alkenyl, alkynyl, cycloalkyl, heterocycloalkyl, aryl or heteroaryl;

$R^5$ is H, OH, alkanyloxy, alkenyloxy, alkynyloxy, O-aryl, alkanyl, alkenyl, alkynyl or aryl;

$R^6$ is H, alkanyl, alkenyl, alkynyl, cycloalkyl, heterocycloalkyl, aryl, heteroaryl, aralkyl, alkanyloxyalkanyl, alkanyloxyalkenyl, alkanyloxyalkynyl, alkenyloxyalkanyl, alkenyloxyalkenyl, alkenyloxyalkynyl, alkynyloxyalkanyl, alkynyloxyalkenyl, alkynyloxyalkynyl, acylalkanyl, (acyloxy)alkanyl, (acyloxy)alkenyl, (acyloxy)alkynyl, non-symmetrical (acyloxy)alkanyldiester, non-symmetrical (acyloxy)alkenyldiester, non-symmetrical (acyloxy)alkynyldiester, or dialkanylphosphate, dialkenylphosphate or dialkynylphosphate;

$R^7$ is H, OH, alkanyl, alkenyl, alkynyl, aryl, alkanyloxy, alkenyloxy, alkynyloxy, —O-aryl, cycloalkyl, heterocycloalkyl, or —O-cycloalkyl, —O-heterocycloalkyl;

$R^8$ is hydrogen, alkanyl, alkenyl or alkynyl;

E is an alkanyl, alkenyl, alkynyl, aryl, heteroaryl, heterocycloalkyl or cycloalkyl group or a fused bi- or tricyclic ring system wherein one phenyl ring is fused to one or two monocyclic cycloalkyl or heterocycloalkyl rings or one bicyclic cycloalkyl or heterocycloalkyl ring, or wherein two phenyl rings are fused to a monocyclic cycloalkyl or heterocycloalkyl ring, wherein monocyclic and bicyclic cycloalkyl and heterocycloalkyl rings are as defined herein, and wherein all of the aforementioned groups may optionally be substituted by one or more substituents R'

Y is hydrogen, halogen, haloalkanyl, haloalkenyl, haloalkynyl, haloalkanyloxy, haloalkenyloxy, haloalkynyloxy, alkanyl, alkenyl, alkynyl, aryl, heteroaryl, heterocycloalkyl or cycloalkyl group or a fused bi- or tricyclic ring system wherein one phenyl ring is fused to one or two monocyclic cycloalkyl or heterocycloalkyl rings or one bicyclic cycloalkyl or heterocycloalkyl ring, or wherein two phenyl rings are fused to a monocyclic cycloalkyl or heterocycloalkyl ring, and wherein all of the aforementioned groups may optionally be substituted by one or more substituents R', or Y is

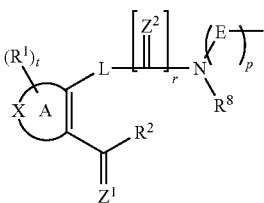

wherein $R^1$, X, A, $Z^1$, $Z^2$, $R^8$, $R^2$, E and p are as defined herein;

m is 0 or 1;
n is 0 or 1;
p is 0 or 1;
q is 0 or 1;
r is 0 or 1;
s is 0 to 2; and
t is 0 to 3;

In another preferred embodiment, the present invention relates to a compound of formula I, wherein A is an aromatic or non-aromatic 5- or 6-membered hydrocarbon ring wherein optionally one or more of the carbon atoms are replaced by a group X, wherein X is independently selected from the group consisting of S, O, N, $NR^4$, $SO_2$ and SO;

L is a single bond

D is O, S, $SO_2$, $NR^4$, or $CH_2$;

$Z^1$ is O, S, or $NR^5$;

$Z^2$ is O, S, or $NR^5$;

$R^1$ independently represents H, halogen, haloalkanyl, haloalkenyl, haloalkynyl, haloalkanyloxy, haloalkenyloxy, haloalkynyloxy, —$CO_2R''$, —$SO_3H$, —OH, —CONR*R'', —CR''O, —$SO_2$—NR*R'', —$NO_2$, —$SO_2$—R'', —SO—R*, —CN, alkanyloxy, alkenyloxy, alkynyloxy, alkanylthio, alkenylthio, alkynylthio, aryl, —NR''—$CO_2$—R', —NR''—CO—R*, —NR''—$SO_2$—R', —O—CO—R*, —O—$CO_2$—R*, —O—CO—NR*R''; cycloalkyl, heterocycloalkyl, alkanylamino, alkenylamino, alkynylamino, hydroxyalkanylamino, hydroxyalkenylamino, hydroxyalkynylamino, —SH, heteroaryl, alkanyl, alkenyl or alkynyl;

R* independently represents H, alkanyl, alkenyl, alkynyl, cycloalkyl, heterocycloalkyl, aminoalkanyl, aminoalkenyl, aminoalkynyl, alkanyloxy, alkenyloxy, alkynyloxy, —OH, —SH, alkanylthio, alkenylthio, alkynylthio, hydroxyalkanyl, hydroxyalkenyl, hydroxyalkynyl, haloalkanyl, haloalkenyl, haloalkynyl, haloalkanyloxy, haloalkenyloxy, haloalkynyloxy, aryl or heteroaryl;

R' independently represents H, —$CO_2R''$, —CONR''R''', —$SO_2NR''$, —NR''—CO-haloalkanyl, haloalkenyl, haloalkynyl, —$NO_2$, —NR''—$SO_2$-haloalkanyl, haloalkenyl, haloalkynyl, —NR''—$SO_2$-alkanyl, —NR''—$SO_2$-alkenyl, —NR''—$SO_2$-alkynyl, —$SO_2$-alkanyl, —$SO_2$-alkenyl, —$SO_2$-alkynyl, —NR''—CO-alkanyl, —NR''—CO-alkenyl, —NR''—CO-alkynyl, —CN, alkanyl, alkenyl, alkynyl, cycloalkyl, heterocycloalkyl, aminoalkanyl, aminoalkenyl, aminoalkynyl, alkanylamino, alkenylamino, alkynylamino, alkanyloxy, alkenyloxy, alkynyloxy, cycloalkyloxy, —OH, —SH, alkanylthio, alkenylthio, alkynylthio, hydroxyalkanyl, hydroxyalkenyl, hydroxyalkynyl, hydroxyalkanylamino, hydroxyalkenylamino, hydroxyalkynylamino, halogen, haloalkanyl, haloalkenyl, haloalkynyl, haloalkanyloxy, haloalkenyloxy, haloalkynyloxy, aryl, aralkyl or heteroaryl;

R'' independently represents hydrogen, haloalkanyl, haloalkenyl, haloalkynyl, hydroxyalkanyl, hydroxyalkenyl, hydroxyalkynyl, alkanyl, alkenyl, alkynyl, cycloalkyl, heterocycloalkyl, aryl, heteroaryl, aminoalkanyl, aminoalkenyl or aminoalkynyl R''' independently represents H or alkanyl $R^2$ is H or $OR^S$, $NHR^7$, $NR^7OR^7$;

or $R^2$ together with the nitrogen atom which is attached to $R^8$ forms a 5 to 7 membered, preferably 5 or 6 membered heteroyclic ring wherein $R^2$ is —$[CH_2]_s$ and $R^8$ is absent;

$R^3$ is H, alkanyl, alkenyl, alkynyl, cycloalkyl, heterocycloalkyl, aryl, alkanyloxy, alkenyloxy, alkynyloxy, —O-aryl; —O-cycloalkyl, —O-heterocycloalkyl, halogen, aminoalkynyl, aminoalkenyl, aminoalkynyl, alkenylamino, alkenylamino, alkynylamino, hydroxylamino, hydroxylalkanyl, hydroxylalkenyl, hydroxylalkynyl, haloalkanyloxy, haloalkenyloxy, haloalkynyloxy, heteroaryl, alkynylthio, alkynylthio, alkynylthio, —S-aryl; —S-cycloalkyl, —S-heterocycloalkyl, aralkyl, haloalkenyl, haloalkenyl or haloalkynyl;

$R^4$ is H, alkanyl, alkenyl, alkynyl, cycloalkyl, heterocycloalkyl, aryl or heteroaryl;

$R^5$ is H, OH, alkanyloxy, alkenyloxy, alkynyloxy, O-aryl, alkanyl, alkenyl, alkynyl or aryl;

$R^6$ is H, alkanyl, alkenyl, alkynyl, cycloalkyl, heterocycloalkyl, aryl, heteroaryl, aralkyl, alkanyloxyalkanyl, alkanyloxyalkenyl, alkanyloxyalkynyl, alkenyloxyalkynyl, alkenyloxyalkenyl, alkenyloxyalkynyl, alkynyloxyalkanyl, alkynyloxyalkenyl, alkynyloxyalkynyl, acylmethyl, (acyloxy)alkanyl, (acyloxy)alkenyl, (acyloxy)alkynyl, non-symmetrical (acyloxy)alkanyldiester, non-symmetrical (acyloxy)alkenyldiester, non-symmetrical (acyloxy)alkynyldiester, or dialkanylphosphate, dialkenylphosphate or dialkynylphosphate;

$R^7$ is H, OH, alkanyl, alkenyl, alkynyl, aryl, alkanyloxy, alkenyloxy, alkynyloxy, —O-aryl, cycloalkyl, heterocycloalkyl, or —O-cycloalkyl, —O-heterocycloalkyl;

$R^8$ is hydrogen, alkanyl, alkenyl or alkynyl;

E is an alkanyl, alkenyl, alkynyl, aryl, heteroaryl, heterocycloalkyl or cycloalkyl group or a fused bi- or tricyclic ring system wherein one phenyl ring is fused to one or two monocyclic cycloalkyl or heterocycloalkyl rings or one bicyclic cycloalkyl or heterocycloalkyl ring, or wherein two phenyl rings are fused to a monocyclic cycloalkyl or heterocycloalkyl ring, wherein monocyclic and bicyclic cycloalkyl and heterocycloalkyl rings are as defined herein, and wherein all of the aforementioned groups may optionally be substituted by one or more substituents R'

Y is hydrogen, halogen, haloalkanyl, haloalkenyl, haloalkynyl, haloalkanyloxy, haloalkenyloxy, haloalkynyloxy, alkanyl, alkenyl, alkynyl, aryl, heteroaryl, heterocycloalkyl or cycloalkyl group or a fused bi- or tricyclic ring system wherein one phenyl ring is fused to one or two monocyclic cycloalkyl or heterocycloalkyl rings or one bicyclic cycloalkyl or heterocycloalkyl ring, or wherein two phenyl rings are fused to a monocyclic cycloalkyl or heterocycloalkyl ring, and wherein all of the aforementioned groups may optionally be substituted by one or more substituents R', or Y is

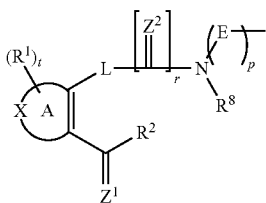

wherein $R^1$, X, A, $Z^1$, $Z^2$, $R^8$, $R^2$, E and p are as defined herein;

m is 0 or 1;
n is 0 or 1;
p is 0 or 1;
q is 0 or 1;
r is 0 or 1;
s is 0 to 2; and
t is 0 to 3;

In another preferred embodiment, the present invention relates to a compound of formula I, wherein A is an aromatic or non-aromatic 5- or 6-membered hydrocarbon ring wherein optionally one or more of the carbon atoms are replaced by a group X, wherein X is independently selected from the group consisting of S, O, N, $NR^4$, $SO_2$ and SO;

L is NH

D is O, S, $SO_2$, $NR^4$, or $CH_2$;

$Z^1$ is O, S, or $NR^S$;

$Z^2$ is O, S, or $NR^5$;

$R^1$ independently represents H, halogen, haloalkynyl, haloalkynyl, haloalkynyl, haloalkanyloxy, haloalkenyloxy, haloalkynyloxy, —$CO_2R''$, —$SO_3H$, —OH, —$CONR*R''$, —CR"O, —$SO_2$—NR*R'', —$NO_2$, —$SO_2$—R'', —SO—R*, —CN, alkanyloxy, alkenyloxy, alkynyloxy, alkanylthio, alkenylthio, alkynylthio, aryl, —NR''—$CO_2$—R', —NR''—CO—R*, —NR''—$SO_2$—R', —O—CO—R*, —O—$CO_2$—R*, —O—CO—NR*R''; cycloalkyl, heterocycloalkyl, alkanylamino, alkenylamino, alkynylamino, hydroxyalkanylamino, hydroxyalkenylamino, hydroxyalkynylamino, —SH, heteroaryl, alkanyl, alkenyl or alkynyl;

R* independently represents H, alkanyl, alkenyl, alkynyl, cycloalkyl, heterocycloalkyl, aminoalkanyl, aminoalkenyl, aminoalkynyl, alkanyloxy, alkenyloxy, alkynyloxy, —OH, —SH, alkanylthio, alkenylthio, alkynylthio, hydroxyalkanyl, hydroxyalkenyl, hydroxyalkynyl, haloalkanyl, haloalkenyl, haloalkynyl, haloalkanyloxy, haloalkenyloxy, haloalkynyloxy, aryl or heteroaryl;

R' independently represents H, —$CO_2R''$, —$CONR''R'''$, —CR"O, —$SO_2NR''$, —NR''—CO-haloalkanyl, haloalkenyl, haloalkynyl, —$NO_2$, —NR''—$SO_2$-haloalkanyl, haloalkenyl, haloalkynyl, —NR''—$SO_2$-alkanyl, —NR''—$SO_2$-alkenyl, —NR''—$SO_2$-alkynyl, —$SO_2$-alkanyl, —$SO_2$-alkenyl, —$SO_2$-alkynyl, —NR''—CO-alkanyl, —NR''—CO-alkenyl, —NR''—CO-alkynyl, —CN, alkanyl, alkenyl, alkynyl, cycloalkyl, heterocycloalkyl, aminoalkanyl, aminoalkenyl, aminoalkynyl, alkanylamino, alkenylamino, alkynylamino, alkanyloxy, alkenyloxy, alkynyloxy, cycloalkyloxy, —OH, —SH, alkanylthio, alkenylthio, alkynylthio, hydroxyalkanyl, hydroxyalkenyl, hydroxyalkynyl, hydroxyalkanylamino, hydroxyalkenylamino, hydroxyalkynylamino, halogen, haloalkanyl, haloalkenyl, haloalkynyl, haloalkanyloxy, haloalkenyloxy, haloalkynyloxy, aryl, aralkyl or heteroaryl;

R'' independently represents hydrogen, haloalkanyl, haloalkenyl, haloalkynyl, hydroxyalkanyl, hydroxyalkenyl, hydroxyalkynyl, alkanyl, alkenyl, alkynyl, cycloalkyl, heterocycloalkyl, aryl, heteroaryl, aminoalkanyl, aminoalkenyl or aminoalkynyl R''' independently represents H or alkanyl $R^2$ is H or $OR^6$, $NHR^7$, $NR^7OR^7$;

or $R^2$ together with the nitrogen atom which is attached to $R^8$ forms a 5 to 7 membered, preferably 5 or 6 membered heteroyclic ring wherein $R^2$ is —$[CH_2]_s$ and $R^8$ is absent;

$R^3$ is H, alkanyl, alkenyl, alkynyl, cycloalkyl, heterocycloalkyl, aryl, alkanyloxy, alkenyloxy, alkynyloxy, —O-aryl; —O-cycloalkyl, —O-heterocycloalkyl, halogen, aminoalkanyl, aminoalkenyl, aminoalkynyl, alkanylamino, alkenylamino, alkynylamino, hydroxylamino, hydroxylalkanyl, hydroxylalkenyl, hydroxylalkynyl, haloalkenyloxy, haloalkenyloxy, haloalkynyloxy, heteroaryl, alkanylthio, alkenylthio, alkynylthio, —S-aryl; —S-cycloalkyl, —S-heterocycloalkyl, aralkyl, haloalkenyl, haloalkenyl or haloalkynyl;

$R^4$ is H, alkanyl, alkenyl, alkynyl, cycloalkyl, heterocycloalkyl, aryl or heteroaryl;

$R^5$ is H, OH, alkanyloxy, alkenyloxy, alkynyloxy, O-aryl, alkanyl, alkenyl, alkynyl or aryl;

$R^6$ is H, alkanyl, alkenyl, alkynyl, cycloalkyl, heterocycloalkyl, aryl, heteroaryl, aralkyl, alkanyloxyalkanyl, alkanyloxyalkenyl, alkanyloxyalkynyl, alkynyloxyalkanyl, alkenyloxyalkenyl, alkenyloxyalkynyl, alkynyloxyalkanyl, alkynyloxyalkanyl, alkynyloxyalkynyl, acylmethyl, (acyloxy)alkanyl, (acyloxy)alkenyl, (acyloxy)alkynyl, non-symmetrical (acyloxy)alkanyldiester, non-symmetrical (acyloxy)alkenyldiester, non-symmetrical (acyloxy)alkynyldiester, or dialkanylphosphate, dialkenylphosphate or dialkynylphosphate;

$R^7$ is H, OH, alkanyl, alkenyl, alkynyl, aryl, alkanyloxy, alkenyloxy, alkynyloxy, cycloalkyl, heterocycloalkyl, or —O-cycloalkyl, —O-heterocycloalkyl;

$R^8$ is hydrogen, alkanyl, alkenyl or alkynyl;

E is an alkanyl, alkenyl, alkynyl, aryl, heteroaryl, heterocycloalkyl or cycloalkyl group or a fused bi- or tricyclic ring system wherein one phenyl ring is fused to one or two monocyclic cycloalkyl or heterocycloalkyl rings or one bicyclic cycloalkyl or heterocycloalkyl ring, or wherein two phenyl rings are fused to a monocyclic cycloalkyl or heterocycloalkyl ring, wherein monocyclic and bicyclic cycloalkyl and heterocycloalkyl rings are as defined herein, and wherein all of the aforementioned groups may optionally be substituted by one or more substituents R'

Y is hydrogen, halogen, haloalkanyl, haloalkenyl, haloalkynyl, haloalkanyloxy, haloalkenyloxy, haloalkynyloxy, alkenyl, alkenyl, alkynyl, aryl, heteroaryl, heterocycloalkyl or cycloalkyl group or a fused bi- or tricyclic ring system wherein one phenyl ring is fused to one or two monocyclic cycloalkyl or heterocycloalkyl rings or one bicyclic cycloalkyl or heterocycloalkyl ring, or wherein two phenyl rings are fused to a monocyclic cycloalkyl or heterocycloalkyl ring, and wherein all of the aforementioned groups may optionally be substituted by one or more substituents R', or Y is ![Chemical structure showing a ring system A with substituents (R¹)ₜ, X, L, Z², R², Z¹, and N-R⁸ with E group]

wherein R¹, X, A, Z¹, Z², R⁸, R², E and p are as defined herein;
m is 0 or 1;
n is 0 or 1;
p is 0 or 1;
q is 0 or 1;
r 1;
s is 0 to 2; and
t is 0 to 3;

In another preferred embodiment, the present invention relates to a compound of formula I, wherein A is an aromatic or non-aromatic 5- or 6-membered hydrocarbon ring wherein optionally one or more of the carbon atoms are replaced by a group X, wherein X is independently selected from the group consisting of S, O, N, $NR^4$, $SO_2$ and SO;

L is a single bond or NH

D is O $Z^1$ is O $Z^2$ is O $R^1$ independently represents H, halogen, haloalkanyl, haloalkanyloxy, —$CO_2R''$, —OH, —CN, alkanyloxy, cycloalkyl, heterocycloalkyl, alkanylamino, heteroaryl, alkanyl;

R* independently represents H, alkanyl, R' independently represents H, cycloalkyl, hydroxyalkanyl, halogen, haloalkanyl, haloalkanyloxy, R'' independently represents hydrogen, alkanyl $R^2$ is H or $OR^6$, $R^3$ is H, $R^4$ is H, alkanyl, cycloalkyl, $R^6$ is H, alkanyl, $R^8$ is hydrogen, alkanyl, E is an alkanyl, aryl, heteroaryl, heterocycloalkyl or cycloalkyl group, wherein all of the aforementioned groups may optionally be substituted by one or more substituents R'

Y is aryl, heteroaryl, heterocycloalkyl or cycloalkyl group wherein all of the aforementioned groups may optionally be substituted by one or more substituents R';

m is 0 or 1;
n is 0 or 1;
q is 0 or 1;
r is 0 or 1; and
t is 0 or 1;

an alkanyl group, if not stated otherwise, denotes a linear or branched $C_1$-$C_6$-alkanyl, preferably a linear or branched chain of one to five carbon atoms; an alkenyl group, if not stated otherwise, denotes a linear or branched $C_2$-$C_6$-alkenyl group comprising one or more carbon-carbon double bonds and which may further comprise one or more carbon carbon single bonds within its hydrocarbon chain; an alkynyl group, if not stated otherwise, denotes a linear or branched $C_2$-$C_6$-alkinyl group comprising one or more carbon-carbon triple bonds and which may further comprise one or more carbon-carbon double and/or single bonds within its hydrocarbon chain, wherein the alkanyl, alkenyl and alkynyl groups can optionally be substituted by one or more substituents $R^9$, preferably by halogen.

The $C_1$-$C_6$-alkanyl, $C_2$-$C_6$-alkenyl and $C_2$-$C_6$-alkynyl residue may preferably be selected from the group comprising —$CH_3$, —$C_2H_5$, —CH=$CH_2$, —C≡CH, —$C_3H_7$, —CH($CH_3$)$_2$, —$CH_2$—CH=$CH_2$, —C($CH_3$)=$CH_2$, —CH=CH—$CH_3$, —C≡C—$CH_3$, —$CH_2$—C≡CH, —$C_4H_9$, —$CH_2$—CH($CH_3$)$_2$, —CH($CH_3$)—$C_2H_5$, —C($CH_3$)$_3$, —$C_5H_{11}$, —C($R^9$)$_3$, —$C_2(R^9)_5$, —$C_2$—C($R^9$)$_3$, —$C_3(R^9)_7$, —$C_2H_4$—C($R^9$)$_3$, —$C_2H_4$—CH=$CH_2$, —CH=CH—$C_2H_5$, —CH=C($CH_3$)$_2$, —$CH_2$—CH=CH—$CH_3$, —CH=CH—CH=$CH_2$, —$C_2H_4$—C≡CH, —C≡C—$C_2H_5$, —$CH_2$—C≡C—$CH_3$, —C≡C—CH=$CH_2$, —CH=CH—C≡CH, —C≡C—C≡CH, —$C_2H_4$—CH($CH_3$)$_2$, —CH($CH_3$)—$C_3H_7$, —$CH_2$—CH($CH_3$)—$C_2H_5$, —CH($CH_3$)—CH($CH_3$)$_2$, —C($CH_3$)$_2$—$C_2H_5$, —$CH_2$—C($CH_3$)$_3$, —$C_3H_6$—CH=$CH_2$, —CH=CH—$C_3H_7$, —$C_2H_4$—CH=CH—$CH_3$, —$CH_2$—CH=CH—$C_2H_5$, —$CH_2$—CH=CH—CH=$CH_2$, —CH=CH—CH=CH—$CH_3$, —CH=CH—$CH_2$—CH=$CH_2$, —C($CH_3$)=CH—CH=$CH_2$, —CH=C($CH_3$)—CH=$CH_2$, —CH=CH—C($CH_3$)=$CH_2$, —$CH_2$—C($CH_3$)=C($CH_3$)$_2$, —$C_3H_6$—C≡H, —C≡C—$C_3H_7$, —$C_2H_4$—C≡C—$CH_3$, —$CH_2$—C≡C—$C_2H_5$, —$CH_2$—C≡C—CH=$CH_2$, —$CH_2$—C≡C—C≡CH, —C≡C—CH=CH—$CH_3$, —CH=CH—C≡C—$CH_3$, —C≡C—C≡C—$CH_3$, —C≡C—$CH_2$—CH=$CH_2$, —CH=CH—$CH_2$—C≡CH, —C≡C—$CH_2$—C≡CH, —C($CH_3$)=CH—CH=$CH_2$, —CH=C($CH_3$)—CH=$CH_2$, —CH=CH—C($CH_3$)=$CH_2$, —C($CH_3$)=CH—C≡CH, —CH=C($CH_3$)—C≡CH, —C≡C—C($CH_3$)=$CH_2$, —$C_3H_6$—CH($CH_3$)$_2$, —$C_2H_4$—CH($CH_3$)—$C_2H_5$, —CH($CH_3$)—$C_4H_9$, —$CH_2$—CH($CH_3$)—$C_3H_7$, —CH($CH_3$)—$CH_2$—CH($CH_3$)$_2$, —CH($CH_3$)—CH($CH_3$)—$C_2H_5$, —$CH_2$—CH($CH_3$)—CH($CH_3$)$_2$, —$CH_2$—C($CH_3$)$_2$—$C_2H_5$, —C($CH_3$)$_2$—$C_3H_7$, —C($CH_3$)$_2$—CH($CH_3$)$_2$, —$C_2H_4$—C($CH_3$)$_3$, —CH($CH_3$)—C($CH_3$)$_3$, —$C_4H_8$—CH=$CH_2$, —CH=CH—$C_4H_9$, —$C_3H_6$—CH=CH—$CH_3$, —$CH_2$—CH=CH—$C_3H_7$, —$C_2H_4$—CH=CH—$C_2H_5$, —$CH_2$—C($CH_3$)=C($CH_3$)$_2$, —$C_2H_4$—CH=C($CH_3$)$_2$, —$C_4H_8$—C≡CH, —C≡C—$C_4H_9$, —$C_3H_6$—C≡C—$CH_3$, —$CH_2$—C≡C—$C_3H_7$, —$C_2H_4$—C≡C—$C_2H_5$, wherein in all of the above-mentioned groups, one or more of the hydrogen atoms can be replaced by a substituent $R^9$, preferably by halogen;

$R^9$ independently represents H, —$CO_2R^{10}$, —$CONR^{10}R^{11}$, —$CR^{10}O$, —$SO_2NR^{10}$, —$NR^{10}$—CO—haloalkanyl, haloalkenyl, haloalkynyl, —$NO_2$, —$NR^{10}$—$SO_2$-haloalkanyl, haloalkenyl, haloalkynyl, —$NR^{10}$—$SO_2$-alkanyl, —$NR^{10}$—$SO_2$-alkenyl, —$NR^{10}$—$SO_2$-alkynyl, —$SO_2$-alkyl, —$SO_2$-alkenyl, —$SO_2$-alkynyl, —$NR^{10}$—CO-alkanyl, —$NR^{10}$—CO-alkenyl, —$NR^{10}$—CO-alkynyl, —CN, alkanyl, alkenyl, alkynyl, cycloalkyl, heterocycloalkyl, aminoalkanyl, aminoalkenyl, aminoalkynyl, alkanylamino, alkenylamino, alkynylamino, alkanyloxy, alkenyloxy, alkynyloxy, cycloalkyloxy, —OH, —SH, alkanylthio, alkenylthio, alkynylthio, hydroxyalkanyl, hydroxyalkenyl, hydroxyalkynyl, hydroxyalkanylamino, hydroxyalkenylamino, hydroxyalkynylamino, halogen, haloalkanyl, haloalkenyl, haloalkynyl, haloalkanyloxy, haloalkenyloxy, haloalkynyloxy, aryl, aralkyl or heteroaryl;

$R^{10}$ independently represents hydrogen, haloalkanyl, haloalkenyl, haloalkynyl, hydroxyalkanyl, hydroxyalkenyl, hydroxyalkynyl, alkanyl, alkenyl, alkynyl, cycloalkyl, heterocycloalkyl, aryl, heteroaryl, aminoalkanyl, aminoalkenyl or aminoalkynyl $R^{11}$ independently represents H or alkanyl.

a cycloalkyl group denotes a monocyclic non-aromatic hydrocarbon ring containing three to eight carbon atoms, preferably four to eight carbon atoms, or a bicyclic non-aromatic hydrocarbon ring system containing seven to ten carbon atoms, preferably eight to ten carbon atoms, wherein the cycloalkyl group optionally comprises one or more double bonds, and wherein the cycloalkyl group is optionally substituted by one or more residues $R^9$ as defined above, and wherein in the cycloalkyl group one or two non-consecutive methylene groups may be replaced by a C=O or C=$NR^7$ group; non-limiting examples of the cycloalkyl group are cyclopropanyl, cyclobutanyl, cyclopentanyl, cyclohexanyl, cycloheptanyl and cyclooctanyl, preferably cyclopentanyl, cyclohexanyl or cycloheptanyl, wherein in the afore-mentioned groups optionally one or more of the hydrogen atoms is replaced by a residue $R^9$ as defined above;

a heterocycloalkyl group denotes a monocyclic non-aromatic hydrocarbon ring containing three to eight carbon atoms, preferably four to eight carbon atoms, or a bicyclic non-aromatic hydrocarbon ring system containing seven to ten carbon atoms, preferably eight to ten carbon atoms, wherein in the heterocycloalkyl group one or more of the carbon atoms of the in the hydrocarbon ring or ring system is replaced by a group selected from the group comprising —N($R^7$)—, —O—, —S—, —S(O)—, —S(O)$_2$—; wherein the heterocycloalkyl group optionally comprises one or more double bonds, and wherein the heterocycloalkyl group is optionally substituted by one or more residues R' as defined above, and wherein in the heterocycloalkyl group one or two methylene groups may be replaced by a C=O or C=$NR^7$ group; non-limiting examples of the heterocycloalkyl group are azepan-1-yl, piperidinyl, in particular piperidin-1-yl and piperidin-4-yl, piperazinyl, in particular N-piperazinyl and 1-alkylpiperazine-4-yl, morpholine-4-yl, tetrahydrofuranyl, tetrahydrothienyl, pyrrolidinyl, tetrahydropyranyl, tetrahydrothiophen, sulfolanyl, sulfolenyl, oxazolinyl, isoxazolinyl, oxazolidinyl, oxazolidinon-yl, wherein in the afore-mentioned groups optionally one or more of the hydrogen atoms is replaced by a residue $R^9$ as defined above;

an alkanyloxy, alkenyloxy or alkynyloxy group denotes an —O-alkanyl, —O-alkenyl or —O-alkynyl group, the alkanyl, alkenyl or alkynyl group being as defined above; the alkanyloxy group is preferably a methoxy, ethoxy, isopropoxy, t-butoxy or pentoxy group;

an alkanylthio, alkenylthio or alkynylthio group denotes an —S-alkanyl, —S-alkenyl or —S-alkynyl group, the alkanyl, alkenyl or alkynyl group being as defined above.

a haloalkanyl, haloalkenyl or haloalkynyl group denotes an alkanyl, alkenyl or alkynyl group which is substituted by one to five halogen atoms, the alkanyl, alkenyl or alkynyl group being as defined above; the haloalkanyl group is preferably a —C($R^{12}$)$_3$, —C$_2$($R^{12}$)$_5$, —CH$_2$—C($R^{12}$)$_3$, —CH$_2$—C($R^{12}$)$_3$, —CH(CH$_2$($R^{12}$))$_2$, —C$_3$($R^{12}$)$_7$ or —C$_2$H$_4$—C($R^{12}$)$_3$, wherein instances of $R^{12}$ may the same or different and each $R^{12}$ is independently selected from F, Cl, Br or I, preferably F;

a hydroxyalkenyl, hydroxyalkenyl or hydroxyalkynyl, group denotes an HO-alkanyl, HO-alkenyl or HO-alkynyl group, the alkanyl, alkenyl or alkynyl group being as defined above;

a haloalkanyloxy, haloalkenyloxy or haloalkynyloxy group denotes an alkanyloxy, alkenyloxy or alkynyloxy group which is substituted by one to five halogen atoms, the alkanyl, alkenyl or alkynyl group being as defined above; the haloalkanyloxy, haloalkenyloxy or haloalkynyloxy group is preferably a —OC($R^{12}$)$_3$, —OC$_2$($R^{12}$)$_5$, —OCH$_2$—C($R^{12}$)$_3$, —OCH(CH$_2$($R^{12}$))$_2$, —OC$_3$($R^{12}$)$_7$ or —OC$_2$H$_4$—C($R^{12}$)$_3$, wherein instances of $R^{12}$ may the same or different and each $R^{12}$ is independently selected from F, Cl, Br or I, preferably F;

a cycloalkyloxy group denotes an —O-cycloalkyl group; the cycloalkynyloxy group is preferably cyclopropoyx, cyclobutoxy and cyclopentoxy a hydroxyalkanylamino, hydroxyalkenylamino or hydroxyalkynylamino group denotes an (HO-alkanyl)$_2$-N—, (HO-alkenyl)$_2$-N— or (HO-alkynyl)$_2$-N— group or HO-alkanyl-NH—, HO-alkenyl-NH— or HO-alkynyl-NH— group, the alkanyl, alkenyl or alkynyl group being as defined above;

an alkanylamino, alkenylamino or alkynylamino group denotes an HN-alkanyl, RN-alkenyl or HN-alkynyl or N-dialkanyl, N-dialkenyl or N-dialkynyl group, the alkanyl, alkenyl or alkynyl group being as defined above;

A halogen group is chlorine, bromine, fluorine or iodine, fluorine being preferred;

an aryl group preferably denotes a mono-, bi-, or tricyclic, preferably monocyclic aromatic hydrocarbon group having six to fifteen carbon atoms, wherein the aryl group is optionally substituted by one or more substituents R', where R' is as defined above; the aryl group is preferably-o-C$_6$H$_4$—R', -m-C$_6$H$_4$—R', -p-C$_6$H$_4$—R', or phenyl, 1-naphthyl, 2-naphthyl, anthracenyl, in particular 1-anthracenyl and 2-anthracenyl group which may optionally be substituted by one or more R', more preferably a phenyl group, -o-C$_6$H$_4$—R', -m-C$_6$H$_4$—R', -p-C$_6$H$_4$—R';

a heteroaryl group denotes a aromatic 5-membered monocyclic aromatic hydrocarbon group wherein at least one of the carbon atoms is replaced by a heteroatom like O, N, S, or a- or a 6-membered monocyclic aromatic hydrocarbon group wherein at least one of the carbon atoms is replaced by an N-atom, S, and wherein the aromatic monocyclic 5- or 6-membered cyclic hydrocarbon group is optionally fused to a further monocyclic 5- to 7-membered, preferably 5- or 6-membered, aromatic or nonaromatic hydrocarbon ring, wherein in the further monocyclic aromatic or nonaromatic hydrocarbon ring one or more, preferably one or two carbon atoms may be replaced by a heteroatom like O, N, S; non-limiting examples of heteroaryl groups are thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, 1H-tetrazol-2-yl, 1H-tetrazol-3-yl, tetrazolyl, indolyl, indolinyl, benzo[b]furanyl, benzo[b]thiophenyl, benzimidazolyl, benzothiazolyl, quinazolinyl, quinoxazolinyl, or preferably quinolinyl, tetrahydroquinolinyl, isoquinolinyl, tetrahydroisoquinolinyl group; the heteroaryl group can optionally be substituted by one or more substituents $R^9$, where $R^9$ is as defined above; the skilled person will acknowledge that in the above definition the replacement of a "carbon atom" by a heteroatom includes any hydrogen atoms bound to said carbon atom;

an aralkyl group denotes an aryl group as defined above which is connected to the molecule of the present invention via an alkanyl, alkenyl or alkynyl bridge, wherein alkanyl, alkenyl or alkynyl is as defined above; preferred aralkyl groups are —CH$_2$—C$_6$H$_5$ (benzyl), —CH$_2$—CH$_2$—C$_6$H$_5$ (phenylethyl), —CH=CH—C$_6$H$_5$, —C≡C—C$_6$H$_5$, -o-CH$_2$—C$_6$H$_4$—R', -m-CH$_2$—C$_6$H$_4$—R', -p-CH$_2$—C$_6$H$_4$—R'; the aralkyl group can optionally be substituted on the aryl and/or alkanyl, alkenyl or alkynyl part by one or more substituents $R^9$, wherein R' is as defined above.

The meaning of E includes alkanyl alkenyl or alkynyl groups optionally substituted by one or more substituents $R^9$, wherein alkanyl alkenyl or alkynyl is defined as above and the meaning of E further includes a cycloalkyl group optionally substituted by one or more substituents $R^9$ such as cyclopropyl, cyclobutyl, cyclopentyl, cyclohexyl, cycloheptyl, cyclooctyl or carbocyclic aromatic groups such as phenyl, 1-naphthyl, 2-naphthyl, anthracenyl, in particular 1-anthracenyl and 2-anthracenyl, and heteroaromatic groups such as N-imidazolyl, 2-imidazolyl, 2-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 4-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl. E also includes fused polycyclic aromatic ring systems such as 9H-thioxanthene-10,10-dioxide in which a carbocyclic aromatic ring or heteroaryl ring is fused to at least one heteroaryl ring.

The meaning of Y includes is hydrogen, halogen, alkanyl, alkenyl, alkynyl, cycloalkyl or O-aralkyl, wherein all of the aforementioned groups may optionally be substituted with one or more R' as defined herein, or alternatively Y is E or —O-E, wherein E is as defined herein; in the aforementioned groups, it is furthermore preferred that optional substituents. R' are halogen. Y can also be

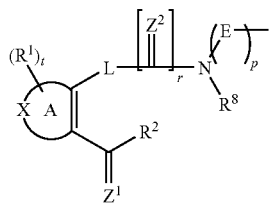

wherein A, X, $R^1$, $R^2$, $R^8$, $Z^1$, $Z^2$ and p have the meaning as defined above.

BRIEF DESCRIPTION OF THE FIGURES

1. Structure of the HCV subgenomic replicon of ET cell line. The HCV replicon ET contains the 5' end of HCV (the HCV Internal Ribosome Entry Site (IRES) and the first few amino acids of the HCV core protein) which drives the production of a firefly luciferase (Luc), ubiquitin (Ubi), and neomycin phosphotransferase ($Neo^R$) fusion protein. Ubiquitin cleavage releases the Luc and $Neo^R$ proteins. The EMCV IRES element controls the translation of the HCV structural proteins NS3-NS5. The NS3 protein cleaves the HCV polyprotein to release the mature NS3, NS4A, NS4B, NS5A and NS5B proteins that are required for HCV replication. At the 3' end of the replicon is the authentic 3' NTR of HCV. The sites of the three cell culture adaptive mutations are shown as arrows (reference 1).

The invention also provides a pharmaceutical composition comprising a compound of formula (I) in free form or in the form of pharmaceutically acceptable salts and physiologically functional derivatives, together with a pharmaceutically acceptable diluent or carrier.

The term "physiologically functional derivative" as used herein refers to compounds which are not pharmaceutically active themselves but which are transformed into their pharmaceutically active form in vivo, i.e. in the subject to which the compound is administered. Examples of physiologically functional derivatives are prodrugs such as those described below in the present application.

As used herein, a prodrug is a derivative of a substance that, following administration, is metabolised in vivo, e.g. by hydrolysis or by processing through an enzyme, into an active metabolite. Prodrugs encompass compounds wherein one or more of the chemical groups of said substance are chemically modified, wherein such modifications are for example: ester, phosphate or sulfate derivatives of hydroxyl groups, ester or amide derivatives of carboxylic groups, imine, amide or urea derivatives of amino groups, and the like.

Moreover, the compounds and compositions according to the present invention can be used preferentially when patients are infected with two different viruses or suffer from viral infections and inflammatory or auto-immune diseases.

SPECIFIC EMBODIMENTS

In certain embodiments A is a 5-membered aromatic hydrocarbon ring wherein one or more, preferably one or two of the carbon atoms are replaced by a group X, wherein X is independently selected from the group consisting of S, O, N or $NR^4$.

In certain embodiments A is selected from the group comprising the following:

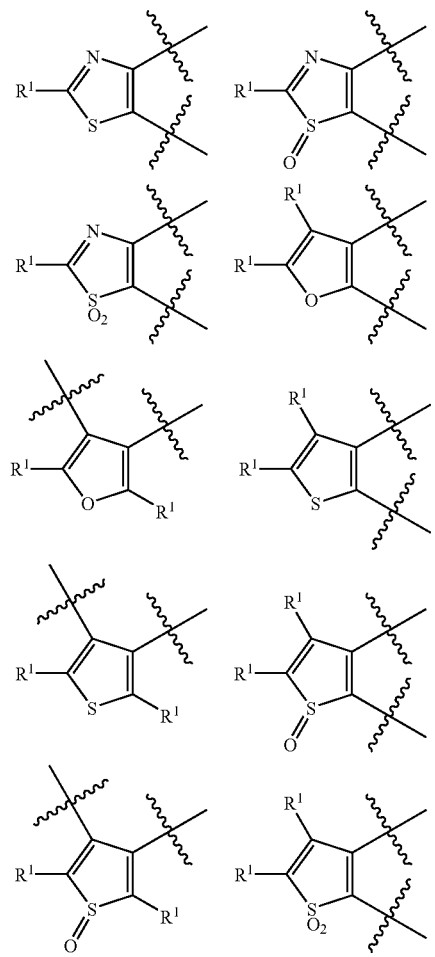

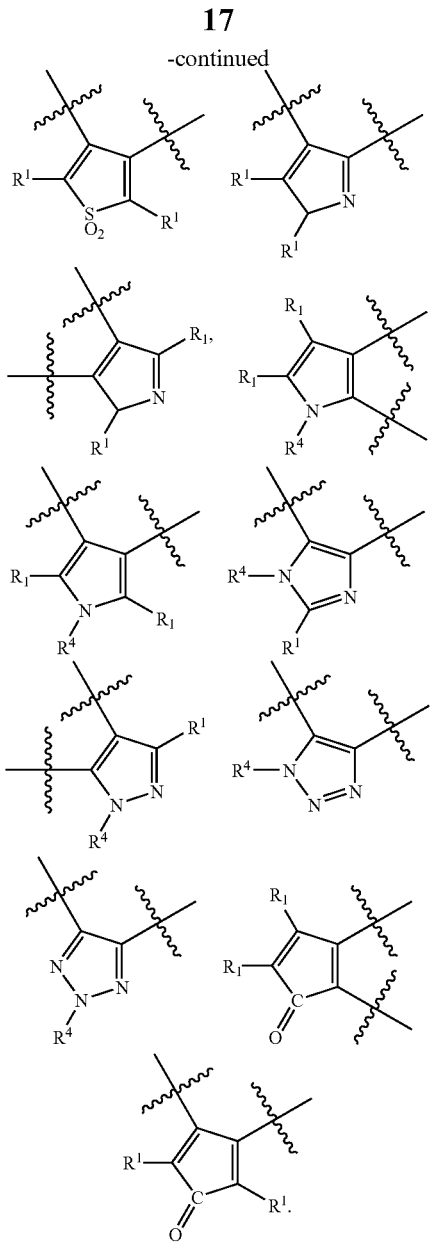

wherein $R^1$ and $R^4$ are defined as above.

In certain embodiments A is a 6-membered aromatic hydrocarbon ring wherein one or more, preferably one or two of the carbon atoms are replaced by a group X, wherein X is independently selected from the group consisting of S, O or N, In certain embodiments A is selected from the group comprising the following:

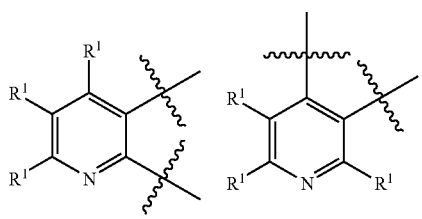

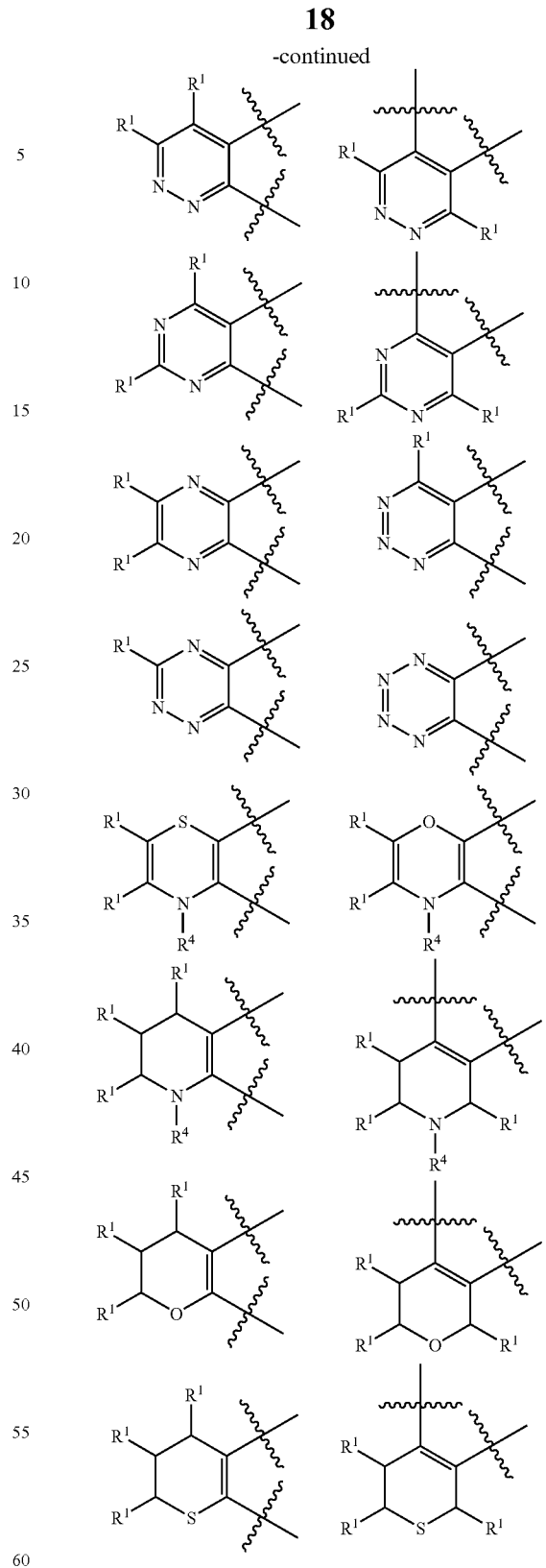

wherein $R^1$ and $R^4$ are defined as above.

In certain embodiments $R^1$ is H, OH, alkanyl, cycloalkyl, halogen, haloalkanyl $CO_2H$ or $SO_3H$ or tetrazole.

In certain embodiments $R^2$ is OH, $NH_2$, NHOH, $NHR^7$, $NR^7OR^7$ or $OR^6$.

In certain embodiments $R^6$ is benzoyloxymethyl, isobutyryloxymethyl, 4-amino-butyryloxymethyl, butyryloxymethyl, 1-(butyryloxy)ethyl, 1-(butyryloxy)-2,2-dimethylpropyl, 1-diethylphosphonooxyethyl, 2-(2-methoxyethoxy)-acetyloxymethyl, p-aminobenzoylmethyl, nicotinyloxymethyl, pivaloyloxymethyl, glutaryloxymethyl, [2-(2-methoxyethoxy)ethoxy]-acetyloxymethyl, 2-(morpholine-4-yl)-ethyl, 1-diethyl-phosphonooxymethyl.

In certain embodiments $R^3$ is H, alkanyl, alkenyl, alkynyl, cycloalkyl, aryl, alkanyloxy, alkenyloxy, alkynyloxy, O-aryl; O-cycloalkyl, halogen, aminoalkanyl, aminoalkenyl, aminoalkynyl, akanylamino, akenylamino, akynylamino, hydroxylamino, haloalkanyl, haloalkenyl, haloalkynyl, hydroxylalkanyl, hydroxylalkenyl, hydroxylalkynyl, haloalkanyloxy, haloalkenyloxy, haloalkynyloxy, heteroaryl, alkanylthio, alkenylthio, alkynylthio, S-aryl; S-cycloalkyl, aralkyl, preferably H.

In certain embodiments $R^4$ is H, alkanyl, alkenyl, alkynyl, cycloalkyl, aryl or heteroaryl, preferably H.

In certain embodiments $R^8$ is H or alkanyl, alkenyl, alkynyl, preferably H or methyl.

In certain embodiments $Z^1$ and $Z^2$ are both O.

In certain embodiments Y is hydrogen, halogen, alkanyl, alkenyl, alkynyl, aryl, heteroaryl, cycloalkyl, heterocycloalkyl or O-aralkyl, wherein all of the aforementioned groups may optionally be substituted with one or more $R^9$ as defined herein, or alternatively Y is E or —O-E, wherein E is as defined herein; in the aforementioned groups, it is furthermore preferred that optional substituents $R^9$ are halogen. Y can also be

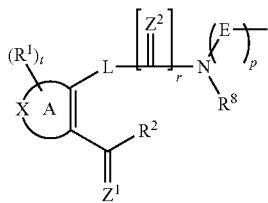

wherein A, X, $R^1$, $R^2$, $R^8$, $Z^1$, $Z^2$ and p have the meaning as defined above. Preferably Y is E as defined herein below and more preferably Y is an optionally substituted phenyl.

In certain embodiments, the fused bi- or tricyclic ring system is a bicyclic ring system wherein one phenyl ring is fused to a 5- or 6-membered cycloalkyl or heterocycloalkyl ring or alternatively a tricyclic ring system wherein two phenyl rings are fused to a 5- or 6-membered cycloalkyl or heterocycloalkyl ring, wherein in the tricyclic ring system preferably the 5- or 6-membered cycloalkyl or heterocycloalkyl ring is placed between the two phenyl rings, more preferably the tricyclic ring system is 9H-thioxanthene-10,10-dioxide, wherein all of the aforementioned groups are optionally substituted by one or more substituents $R^9$.

In certain embodiments E is an alkyl or cycloalkyl group, preferably selected from the group comprising methyl, ethyl, propy, butyl, cyclopropyl, cyclobutyl, cyclopentyl, cyclohexyl, cycloheptyl or cyclooctyl, wherein all of the aforementioned groups are optionally substituted by one or more substituents $R^9$.

In certain embodiments E is an aryl or heteroaryl group selected from the group comprising phenyl, 1-naphthyl, 2-naphthyl, anthracenyl, in particular 1-anthracenyl and 2-anthracenyl, N-imidazolyl, 2-imidazolyl, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 4-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl, wherein all of the aforementioned groups are optionally substituted by one or more substituents $R^9$.

In certain embodiments E is a fused bi- or tricyclic ring system, which is optionally substituted by one or more substituents $R^9$, preferably a 9H-thioxanthene-10,10-dioxide group, which is optionally substituted by one or more substituents $R^9$.

In certain embodiments $R^9$ is selected from the group comprising cyano, nitro, halogen, alkanyloxy, alkenyloxy, alkynyloxy, cycloalkyloxy, haloalkanyl, haloalkenyl, haloalkynyl, haloalkanyloxy, haloalkenyloxy, haloalkynyloxy, cycloalkyl, hetreocycloalkyl, heteroaryl, alkanyl, alkenyl, alkynyl or aryl, preferably $R^9$ is Br, F, Cl, $CF_3$, $OCF_3$, —CN, cyclopropoxy, cyclobutoxy, isopropoxy, ethoxy or methoxy.

In certain embodiments the heteroaryl group is selected from the group comprising imidazolyl, thienyl, furanyl, pyridyl, pyrimidyl, pyranyl, pyrazolyl, pyrazinyl, thiazolyl, 1H-tetrazol-2-yl, 1H-tetrazol-3-yl, or oxazolyl.

In certain embodiments t is 0, 1 or 2.

In certain embodiments s is 0 or 1.

In certain embodiments m=1 and D is O, S, $SO_2$, $NR^4$, or $CH_2$, preferably S or O, more preferably O.

In certain embodiments m=0.

In certain embodiments q=0.

In certain embodiments n=0.

In certain embodiments r is 0 or 1.

In certain embodiments L is a single bond.

In certain embodiments q=1, m=1 and n=1, wherein preferably D=O and/or $R^3$=H).

In certain embodiments $R^8$=H.

In certain embodiments A is cyclopenten, thiophen, thiaziol or dihydrothiophen.

In certain embodiments —(C=$Z^1$)—$R^2$ is COOH.

In certain embodiments $R^1$=H.

In certain embodiments Y is hydrogen, halogen, haloalkanyl, haloalkenyl, haloalkynyl, haloalkanyloxy, haloalkenyloxy, haloalkynyloxy, alkanyl, alkenyl, alkynyl, cycloalkyl or B, preferably F, $CF_3$, $OCF_3$, or phenyl, optionally substituted by one or more substituents $R^9$, more preferably phenyl, optionally substituted by one or more F, Cl, methoxy, $CF_3$, or $OCF_3$.

In certain embodiments q=1 and n=0 or 1 and m=1 and D is preferably O.

In further particularly preferred embodiment, in compounds of formula (I), D=O (thus m=1), n=0, q=1, t=1, $Z^1$=O, $Z^2$O, and E is phenylene which is either unsubstituted or substituted with Cl, F and/or $CF_3$ or $OCF_3$, and Y is phenyl which is also either unsubstituted or substituted with Cl, F and/or $CF_3$, $OCH_3$, $OCH_2CH_3$, or $OCF_3$, and A is an aromatic hydrocarbon ring, wherein a carbon is replaced by S.

In further particularly preferred embodiment, in compounds of formula (I), D=S (thus m=1), n=0, q=1, t=1, $Z^1$=O, $Z^2$=O (thus r=1), and E is phenylene which is either unsubstituted or substituted with Cl, F and/or $CF_3$ or $OCF_3$, and Y is phenyl which is also either unsubstituted or substituted with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), D=O (thus m=1), $R^3$ is H (thus n=1), q=1, t=1, $Z^1$=O, $Z^2$=O, and E is phenylene which is either unsubstituted or substituted with Cl, F and/or $CF_3$ or $OCF_3$, and Y is phenyl which is also either unsubstituted or substituted with Cl, F and/or CF$_3$, OCH$_3$, OCH$_2$CH$_3$, or OCF$_3$, and A is an aromatic hydrocarbon ring, wherein a carbon is replaced by O.

In a further particularly preferred embodiment, in compounds of formula (I), D=O (thus m=1), n=0, q=1, t=1, Z$^1$=O, Z$^2$=O, and E is phenylene which is either unsubstituted or substituted with Cl, F and/or CF$_3$ or OCF$_3$, and Y is phenyl which is also either unsubstituted or substituted with Cl, F and/or CF$_3$, OCH$_3$, OCH$_2$CH$_3$, or OCF$_3$, and A is an aromatic hydrocarbon ring, wherein a carbon is replaced by O.

In a further particularly preferred embodiment, in compounds of formula (I), D=S (thus m=1), n=0, q=1, t=1, Z$^1$=O, Z$^2$=O (thus r=1), and E is phenylene which is either unsubstituted or substituted with Cl, F and/or CF$_3$ or OCF$_3$, and Y is phenyl which is also either unsubstituted or substituted with Cl, F and/or CF$_3$, OCH$_3$, OCH$_2$CH$_3$, or OCF$_3$, and A is an aromatic hydrocarbon ring, wherein a carbon is replaced by O.

In further particularly preferred embodiment, in compounds of formula (I), D=O (thus m=1), n=0, q=1, t=1, Z$^1$=O, Z$^2$=O, and E is phenylene which is either unsubstituted or substituted with Cl, F and/or CF$_3$ or OCF$_3$, and Y is phenyl which is also either unsubstituted or substituted with Cl, F and/or CF$_3$, OCH$_3$, OCH$_2$CH$_3$, or OCF$_3$, and A is a five membered aromatic ring, wherein one carbon atom is replaced by O.

In a further particularly preferred embodiment, in compounds of formula (I), D=S (thus m=1), n=0, q=1, t=1, Z$^1$=O, Z$^2$=O, and E is phenylene which is either unsubstituted or substituted with Cl, F and/or CF$_3$ or OCF$_3$, and Y is phenyl which is also either unsubstituted or substituted with Cl, F and/or CF$_3$, OCH$_3$, OCH$_2$CH$_3$, or OCF$_3$, and A is a five membered aromatic ring wherein one carbon atom is replaced by O.

In a further particularly preferred embodiment, in compounds of formula (I), D=O (thus m=1), n=0, q=1, t=1, Z$^1$=O, Z$^2$=O, and E is phenylene which is either unsubstituted or substituted with Cl, F and/or CF$_3$ or OCF$_3$, and Y is phenyl which is also either unsubstituted or substituted with Cl, F and/or CF$_3$, OCH$_3$, OCH$_2$CH$_3$, or OCF$_3$, and A is a five membered aromatic ring, wherein one carbon atom is replaced by S.

In a further particularly preferred embodiment, in compounds of formula (I), D-S (thus m=1), n=0, q=1, t=1, Z$^1$=O, Z$^2$=O, and E is phenylene which is either unsubstituted or substituted with Cl, F and/or CF$_3$, OCH$_3$, OCH$_2$CH$_3$, or OCF$_3$, and Y is phenyl which is either unsubstituted or substituted with Cl, F and/or CF$_3$ or OCF$_3$, and A is a five membered aromatic ring, wherein one carbon atom is replaced by S.

In a further particularly preferred embodiment, in compounds of formula (I), Z$^1$=O, Z$^2$=O, q=0 or 1, t=2, E is phenylene which is either unsubstituted or substituted with Cl, F and/or CF$_3$, OCH$_3$, OCH$_2$CH$_3$, or OCF$_3$, and Y is phenyl which is also either unsubstituted or substituted with Cl, F and/or CF$_3$ or OCF$_3$, and R$^2$ together with the nitrogen atom which is attached to R$^8$ form a 6 membered heterocyclic ring with the proviso that R$^2$ is —[CH$_2$]$_s$ and R$^8$ is absent; and A is furan.

In a further particularly preferred embodiment, in compounds of formula (I), Z$^1$=O, Z$^2$=O, q=0 or 1, t=2, E is phenylene which is either unsubstituted or substituted with Cl, F and/or CF$_3$, OCH$_3$, OCH$_2$CH$_3$, or OCF$_3$, and Y is H or F, and R$^2$ together with the nitrogen atom which is attached to R$^8$ form a 6 membered heterocyclic ring with the proviso that R$^2$ is —[CH$_2$]$_s$ and R$^8$ is absent; and A is furan.

In a further particularly preferred embodiment, in compounds of formula (I), L=single bond, Z$^1$=O (thus r=1), Z$^2$=O, q=0, t=1, R$^2$=OH, R$^8$=H and E is phenylene which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by S.

In a further particularly preferred embodiment, in compounds of formula (I), L=single bond, Z$^1$=O (thus r=1), Z$^2$=O, q=0, t=1, R$^2$=OH, R$^8$=H and E is phenylene which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by S.

In a further particularly preferred embodiment, in compounds of formula (I), L=single bond, Z$^1$=O (thus r=1), Z$^2$=O, q=0, t=1, R$^2$=OH, R$^8$=H and E is heteroaryl which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by S.

In a further particularly preferred embodiment, in compounds of formula (I), L=single bond, Z$^1$=O (thus r=1), Z$^2$=O, q=0, t=1, R$^2$=OH, R$^8$=H and E is heteroaryl which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by S.

In a further particularly preferred embodiment, in compounds of formula (I), L=single bond, Z$^1$=O (thus r=1), Z$^2$=O, q=0, t=1, R$^2$=OH, R$^8$=H and E is phenylene which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by S.

In a further particularly preferred embodiment, in compounds of formula (I), L=single bond, Z$^1$=O (thus r=1), Z$^2$=O, q=0, t=1, R$^2$=OH, R$^8$=H and E is phenylene which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by S.

In a further particularly preferred embodiment, in compounds of formula (I), L=single bond, Z$^1$=O (thus r=1), Z$^2$=O, q=0, t=1, R$^2$=OH, R$^8$=H and E is heteroaryl which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by S.

In a further particularly preferred embodiment, in compounds of formula (I), L=single bond, Z$^1$=O (thus r=1), Z$^2$=O, q=0, t=1, R$^2$=OH, R$^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L-single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=single bond, $Z^1$=O (thus r=1), $Z^2$=O, q=0, t=1, $R^2$=OH, $R^8$=H and E is phenyl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=single bond, $Z^1$=O (thus r=1), $Z^2$=O, q=0, t=1, $R^2$=OH, $R^8$=H and E is phenyl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=single bond, $Z^1$=O (thus r=1), $Z^2$=O, q=0, t=1, $R^2$=OH, $R^8$=H and E is heteroaryl is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a further particularly preferred embodiment, in compounds of formula (I), L=single bond, $Z^1$=O (thus r=1), $Z^2$=O, q=0, t=1, $R^2$=OH, $R^8$=H and E is phenylene which either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $NR^4$.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $NR^4$.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $NR^4$.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $NR^4$.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted with Cl, F and/or $CF_3$, $OCH_3$, $OCH_2CH_3$, or $OCF_3$, and Y is heteroaryl which is also either unsubstituted or substituted with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (1), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $NR^4$.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a wherein a carbon is replaced by $NR^4$.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $NR^4$.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $NR^4$.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=single bond, r=0, $Z^2$=O, q=0, t=1, $R^2$=OH, $R^8$=H and E is heteroaryl which is either or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=single bond, r=0, $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=single bond, r=0, $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=single bond, r=0, $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=single bond, r=0, $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I L=single bond, r=0, $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=single bond, r=0, $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=single bond, r=0, $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=single bond, r=0, $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I L=single bond, r=0, $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or $CF_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (1), L=single bond, r=0, $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=single bond, r=0, $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=single bond, r=0, $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by N.

In a further particularly preferred embodiment, in compounds of formula (I), L=single bond, r=0, Z$^2$=O, q=0, t=1, R$^2$=H, R$^8$=H and E is phenylene which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by N.

In a further particularly preferred embodiment, in compounds of formula (I), L=single bond, r=0, Z$^2$=O, q=0, t=1, R$^2$=OH, R$^8$=H and E is heteroaryl which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by N.

In a further particularly preferred embodiment, in compounds of formula (I), L=single bond, r=0, Z$^2$=O, q=0, t=1, R$^2$=OH, R$^8$=H and E is heteroaryl which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by N.

In a further particularly preferred embodiment, in compounds of formula (I), L=single bond, r=0, Z$^2$=O, q=0, t=1, R$^2$=OH, R$^8$=H and E is phenylene which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by N.

In a further particularly preferred embodiment, in compounds of formula (I), L=single bond, r=0, Z$^2$=O, q=0, t=1, R$^2$=OH, R$^8$=H and E is phenylene which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by N.

In a further particularly preferred embodiment, in compounds of formula (I), L=single bond, r=0, Z$^2$=O, q=0, t=1, R$^2$=OH, R$^8$=H and E is heteroaryl which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by N.

In a further particularly preferred embodiment, in compounds of formula (I), L=single bond, r=0, Z$^2$=O, q=0, t=1, R$^2$=OH, R$^8$=H and E is heteroaryl which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by N.

In a further particularly preferred embodiment, in compounds of formula (I), L=single bond, r=0, Z$^2$=O, q=0, t=1, R$^2$=OH, R$^8$=H and E is phenylene which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by NR$^4$.

In a further particularly preferred embodiment, in compounds of formula (I), L=single bond, Z$^2$=O, q=0, t=1, R$^2$=OH, R$^8$=H and E is phenylene which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by NR$^4$.

In a further particularly preferred embodiment, in compounds of formula (I), L=single bond, r=0, Z$^2$=O, q=0, t=1, R$^2$=OH, R$^8$=H and E is heteroaryl which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by NR$^4$.

In a further particularly preferred embodiment, in compounds of formula (I), L=single bond, r=0, Z$^2$=O, q=0, t=1, R$^2$=OH, R$^8$=H and E is heteroaryl which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by NR$^4$.

In a further particularly preferred embodiment, in compounds of formula (I), L=single bond, R=0, Z$^2$=O, q=0, t=1, R$^2$=OH, R$^8$=H and E is phenylene which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by NR$^4$.

In a further particularly preferred embodiment, in compounds of formula (I), L=single bond, r=0, Z$^2$=O, q=0, t=1, R$^2$=OH, R$^8$=H and E is phenylene which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by NR$^4$.

In a further particularly preferred embodiment, in compounds of formula (I), L=single bond, r=0, Z$^2$=O, q=0, t=1, R$^2$=OH, R$^8$=H and E is heteroaryl which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by NR$^4$.

In a further particularly preferred embodiment, in compounds of formula (I), L=single bond, r=0, Z$^2$=O, q=0, t=1, R$^2$=OH, R$^8$=H and E is heteroaryl which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by NR$^4$.

In a further particularly preferred embodiment, in compounds of formula (I), L=single bond, Z$^1$=O (thus r=1), Z$^2$=O, q=0, t=1, R$^2$=H, R$^8$=H and E is phenylene which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by SO.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=NH, $Z^1$=O (thus r=1), $Z^2$=O, q=0, t=1, $R^2$=OH, $R^8$=H and F is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=single bond, r=0, $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=single bond, r=0, (thus r=1), $Z^2$=O, q=0, t=1, $R^2$=OH, $R^8$=H and E is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=single bond, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=single bond, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (1), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/ or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=NH, $Z^1$=O (thus r=1), $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=NH, $Z^1$=O (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=single bond, r=0, $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=single bond, r=0, $Z^2$=O, q=0, t=1, $R^2$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=single bond, r=0, (thus r=1), $Z^2$=O, q=0, t=1, $R^2$=OH, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=OH, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=OH, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is phenyl which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a non-aromatic hydrocarbon ring.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is phenyl which is either unsubstituted or substituted preferably with Cl, F and/or, CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is an aromatic hydrocarbon ring.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a non-aromatic hydrocarbon ring.

In a further particularly preferred embodiment, in compounds of formula (I), L=single bond, $Z^1$=O (thus r=1), D=O, m=1, n=1, q=1, t=1, $R^2$=OH, $R^3$=H, $R^8$=H and E is heteroaryl which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is an aromatic hydrocarbon ring.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=OH, $R^8$=H and E is phenyl which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is a non-aromatic hydrocarbon ring.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H, and E is phenyl which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is an aromatic hydrocarbon ring.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is a non-aromatic hydrocarbon ring.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is an aromatic hydrocarbon ring.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a aromatic hydrocarbon ring, wherein a carbon is replaced by O.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by O.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or CF$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by O.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by O.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by O.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by O.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by O.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by O.

In a further particularly preferred embodiment, in compounds of formula (I), L=single bond, Z$^1$=O (thus r=1), Z$^2$=O, D=O, m=1, n=1, q=1, t=1, R$^2$=OH, R$^3$=H, R$^8$=H and E is phenylene which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by N.

In a further particularly preferred embodiment, in compounds of formula (I), L=single bond, Z$^1$=O (thus r=1), Z$^2$=O, D=O, m=1, n=1, q=1, t=1, R$^2$=OH, R$^3$=H, R$^8$=H and E is phenylene which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by N.

In a further particularly preferred embodiment, in compounds of formula (I), L=single bond, Z$^1$=O (thus r=1), Z$^2$=O, D=O, m=1, n=1, q=1, t=1, R$^2$=OH, R$^3$=H, R$^8$=H and E is heteroaryl which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by N.

In a further particularly preferred embodiment, in compounds of formula (I), L=single bond, Z$^1$=O (thus r=1), Z$^2$=O, D=O, m=1, n=1, q=1, t=1, R$^2$=OH, R$^3$=H, R$^8$=H and E is heteroaryl which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by N.

In a further particularly preferred embodiment, in compounds of formula (I), L=single bond, Z$^1$=O (thus r=1), Z$^2$=O, D=O, m=1, n=1, q=1, t=1, R$^2$=OH, R$^3$=H, R$^8$=H and E is phenylene which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by N.

In a further particularly preferred embodiment, in compounds of formula (I), L=single bond, Z$^1$=O (thus r=1), Z$^2$=O, D=O, m=1, n=1, q=1, t=1, R$^2$=OH, R$^3$=H, R$^8$=H and E is phenylene which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by N.

In a further particularly preferred embodiment, in compounds of formula (I), L=single bond, Z$^1$=O (thus r=1), Z$^2$=O, D=O, m=1, n=1, q=1, t=1, R$^2$=OH, R$^3$=H, R$^8$=H and E is heteroaryl which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by N.

In a further particularly preferred embodiment, in compounds of formula (I), L=single bond, Z$^1$=O (thus r=1), Z$^2$=O, D=O, m=1, n=1, q=1, t=1, R$^2$=OH, R$^3$=H, R$^8$=H and E is heteroaryl which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by N.

In a further particularly preferred embodiment, in compounds of formula (I), L=single bond, Z$^1$=O (thus r=1), Z$^2$=O, D=O, m=1, n=1, q=1, t=1, R$^2$=OH, R$^3$=H, R$^8$=H and E is phenylene which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by NR$^4$.

In a further particularly preferred embodiment, in compounds of formula (I), L=single bond, Z$^1$=O (thus r=1), Z$^2$=O, D=O, m=1, n=1, q=1, t=1, R$^2$=OH, R$^3$=H, R$^8$=H and E is phenylene which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by NR$^4$.

In a further particularly preferred embodiment, in compounds of formula (I), L=single bond, Z$^1$=O (thus r=1), Z$^2$=O, D=O, m=1, n=1, q=1, t=1, R$^2$=OH, R$^3$=H, R$^8$=H and E is heteroaryl which is either unsubstituted or substituted preferably with Cl, F and/or CF$_3$, OCH$_2$CH$_3$, or OCF$_3$, and Y is phenyl which is also either substituted preferably with Cl, F and/or CF$_3$, OCH$_3$, OCH$_2$CH$_3$, or OCF$_3$, and A is an aromatic hydrocarbon ring, wherein a carbon is replaced by NR$^4$.

In a further particularly preferred embodiment, in compounds of formula (I), L=single bond, Z$^1$=O (thus r=1), Z$^2$=O, D=O, m=1, n=1, q=1, t=1, R$^2$=OH, R$^3$=H, R$^8$=H and E is heteroaryl which is either unsubstituted or substituted preferably with Cl, F and/or CF$_3$, OCH$_3$, OCH$_2$CH$_3$, or OCF$_3$, and Y is phenyl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by NR$^4$.

In a further particularly preferred embodiment, in compounds of formula (I), L=single bond, Z$^1$=O (thus r=1), Z$^2$=O, D=O, m=1, n=1, q=1, t=1, R$^2$=phenylene which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is an aromatic hydrocarbon ring, wherein a carbon is replaced by NR$^4$.

In a further particularly preferred embodiment, in compounds of formula (I), L=single bond, Z$^1$=O (thus r=1), Z$^2$=O, D=O, m=1, n=1, q=1, t=1, R$^2$=OH, R$^3$=H, R$^8$=OH and E is phenylene which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or CF$_3$, OCH$_3$, OCH$_2$CH$_3$, or OCF$_3$, and A is a non-aromatic hydrocarbon ring, wherein a carbon is replaced by NR$^4$.

In a further particularly preferred embodiment, in compounds of formula (I), L=single bond, Z$^1$=O (thus r=1), Z$^2$=O, D=O, m=1, n=1, q=1, t=1, R$^2$=OH, R$^3$=H, R$^8$=OH and E is heteroaryl which is either unsubstituted or substituted preferably with Cl, F and/or CF$_3$, OCH$_3$, OCH$_2$CH$_3$, or OCF$_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=OH and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $NR^4$.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (1), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $NR^4$.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $NR^4$.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $NR^4$.

In a further particularly preferred embodiment, in compounds of formula (I), $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a further particularly preferred embodiment, in compounds of formula (I), $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_2CH_3$, or $OCF_3$, and A is a non-aromatic hydrocarbon ring, wherein a carbon is replaced by $NR^4$.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and e is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by S.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by S.

In a further particularly preferred embodiment, in compounds of formula (I), L=single bond, r=0, $Z^2$=O, D=O, m=1, n=1, q=1, t=1, $R^2$=OH, $R^3$=H, $R^8$H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring.

In a further particularly preferred embodiment, in compounds of formula (I), L-single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I L-single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by O.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by O.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by N.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by N.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $NR^4$.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a farther particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $NR^4$.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $NR^4$.

In a further particularly preferred embodiment, in compounds of formula (1), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is an aromatic hydrocarbon ring, wherein a carbon is replaced by $NR^4$.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $NR^4$.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$ H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=NH, $Z^1$=O (thus r=1), $Z^2$=O, q D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=single bond, r=0, (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by SO.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=single bond, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=NH, $Z^1$=O (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is phenyl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=single bond, r=0, $Z^2$=O, D=O, m=1, n=1, q=1, t=1, $R^2$=OH, $R^3$=H, $R^8$=H and E is phenylene which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

In a further particularly preferred embodiment, in compounds of formula (I), L=single bond, r=0, (thus r=1), $Z^2$=O, D=O, m=1, n=1, q=1, t=1, $R^2$=OH, $R^3$=H, $R^8$=H and E is heteroaryl which is either unsubstituted or substituted preferably with Cl, F and/or $CF_3$, $OCH_3$, $OCH_2CH_3$, or $OCF_3$, and Y is heteroaryl which is also either unsubstituted or substituted preferably with Cl, F and/or $CF_3$, $OCH_3$, $OCH_2CH_3$, or $OCF_3$, and A is a non-aromatic hydrocarbon ring, wherein a carbon is replaced by $SO_2$.

Exemplary compounds according to this invention may include any one selected from:
1. 3-(2,3,5,6-Tetrafluoro-3'-trifluoromethoxy-biphenyl-4-yl-carbamoyl)-thiophene-2-carboxylic acid
2. 4-(2'-Chloro-3,5-difluoro-biphenyl-4-ylcarbamoyl)-2,5-dihydro-thiophene-3-carboxylic acid
3. 2-[3-Chloro-4-(2-chloro-6-fluoro-benzyloxy)-phenylcarbamoyl]-cyclopent-1-enecarboxylic acid
4. 2-(2,3,5,6-Tetrafluoro-3'-trifluoromethoxy-biphenyl-4-yl-carbamoyl)-cyclopent-1-enecarboxylic acid
5. 2-[4-(2-Chloro-6-fluoro-benzyloxy)-3-fluoro-phenylcarbamoyl]-cyclopent-1-enecarboxylic acid
6. 2-(3-Fluoro-3'-methoxy-biphenyl-4-ylcarbamoyl)-cyclopent-1-enecarboxylic acid
7. 2-(3-biphenyl-4-ylureido)benzoic acid
8. 2-(2,3,5,6-tetrafluoro-3'-methoxybiphenyl-4-ylcarbamoyl)furan-3-carboxylic acid
9. 4-(3'-ethoxy-3,5-difluorobiphenyl-4-ylcarbamoyl)thiophene-3-carboxylic acid
10. 2-(2,3,5,6-tetrafluoro-3'-methoxybiphenyl-4-ylcarbamoyl)cyclopent-1-enecarboxylic acid
11. 2-(2,3,5,6-tetrafluoro-2'-methoxybiphenyl-4-ylcarbamoyl)cyclopent-1-enecarboxylic acid
12. 2-(3,5-difluoro-3'-(trifluoromethoxy)biphenyl-4-ylcarbamoyl)cyclopent-1-enecarboxylic acid
13. 3-hydroxy-2-(2,3,5,6-tetrafluoro-3'-(trifluoromethoxy)biphenyl-4-ylcarbamoyl)cyclopent-1-enecarboxylic acid
14. 2-(2-chloro-4'-methoxybiphenyl-4-ylcarbamoyl)cyclopent-1-enecarboxylic acid
15. 4-(3,5-difluoro-3'-(trifluoromethoxy)biphenyl-4-ylcarbamoyl)thiophene-3-carboxylic acid
16. 5-(4-(2-chloro-6-fluorobenzyloxy)-3-fluorophenylcarbamoyl)cyclopenta-1,4-dienecarboxylic acid
17. 3-(3,5-difluoro-3'-(trifluoromethoxy)biphenyl-4-ylcarbamoyl)thiophene-2-carboxylic acid
18. 2-(3-fluoro-3'-methoxybiphenyl-4-ylamino)nicotinic acid
19. 2-(3,5-difluoro-3'-methoxybiphenyl-4-ylamino)nicotinic acid
20. 5-cyclopropyl-2-(5-methyl-6-(3-(trifluoromethoxy)phenyl)pyridin-3-ylamino)benzoic acid
21. 2-[4-(2-Chloro-6-fluoro-benzyloxy)-3-fluoro-phenylcarbamoyl]-cyclopent-1-enecarboxylic acid
22. 2-[3,5-Dichloro-4-(2-chloro-6-fluoro-benzyloxy)-phenylcarbamoyl]-cyclopent-1-enecarboxylic acid
23. 2-(2-Chloro-4'-dimethylamino-biphenyl-4-ylcarbamoyl)-cyclopent-1-enecarboxylic acid
24. 3-(3-Fluoro-3'-methoxy-biphenyl-4-ylcarbamoyl)-thiophene-2-carboxylic acid
25. 4-(2,3,5,6-Tetrafluoro-3'-trifluoromethoxy-biphenyl-4-ylcarbamoyl)-2,5-dihydro-thiophene-3-carboxylic acid
and the salts thereof.

The skilled person will appreciate that the present invention does not encompass compounds comprising chemically unstable entities, such as for instance ozone groups or groups containing pentavalent carbon atoms or trivalent oxygen atoms, and the like. Accordingly, combinations or variations of the chemical groups and moieties described herein which lead to such chemically unstable entities are excluded.

The cycloalkyl, heterocycloalkyl, aryl, heteroaryl, alkanyl, alkenyl, alkynyl groups and groups derived from alkanyl, alkenyl or alkynyl (such as for instance alkanyloxy) as defined herein, irrespective of a possible substitution with one or more residues R', may be a terminal group on a side chain branch of the compounds of the present invention or may be placed in within a side chain branch of the compounds of the present invention. Accordingly, in the context of the present invention, the above-mentioned terms encompass cycloalkylene, heterocycloalkylene, arylene, heteroarylene, alkanylene, alkenylene, alkynylene groups and groups derived from alkanylene, alkenylene or alkynylene.

In the compounds of the present invention, the residues R' and R" preferably may not be substituted by a group comprising a second or otherwise further residue selected from R' and/or R". This is to be understood such that compounds comprising oligomeric or polymeric side chains comprising multiple R' and/or R" units are preferably not encompassed by the present invention.

It is to be understood that the specific embodiments described above may be combined in any suitable and chemically reasonable fashion to furnish further specific embodiments.

Due to their favourable pharmacokinetic properties, the compounds of the present invention are suited for oral treatment regimen wherein the medicament comprising the compound according to the present invention is administered once daily.

In one embodiment, the compounds of the present invention are for the treatment or amelioration of a disease or medical condition caused by HIV.

In one embodiment, the compounds of the present invention are for the treatment or amelioration of a disease or medical condition caused by HBV.

In one embodiment, the compounds of the present invention are for the treatment or amelioration of a disease or medical condition caused by HCV.

In one embodiment, the compounds of the present invention are for the treatment or amelioration of a disease or medical condition caused by HPMV.

In one embodiment, the compounds of the present invention are for the prevention of transplant rejection due to viral infections, e.g. the rejection of liver transplants due to HCMV, HBV or HCV infection.

In one embodiment, the compounds of the present invention are for the treatment of patients co-infected with multiple viruses, e.g. co-infected with HIV/HBV or HIV/HCV.

In one embodiment, the compounds of the present invention are applied in combination therapy with interferones, such as interferone α or pegylated interferon α.

Preferably, the compounds according to the invention have a half-maximal inhibitory concentration ($IC_{50}$) of 1 μM or less, more preferably 200 nM or less, and even more preferably 20 nM or less for the inhibition of dihydroorotate-dehydrogenase in an in vitro assay and a half-maximal effective concentration ($EC_{50}$) of 10 μM or less, preferably 1 μM or less and even more preferably 200 nM or less for inhibition of viruses in an in vitro assay.

Preferably, the compounds according to the invention have a solubility in water of 5 μg or greater, preferably 10 μg/mL or greater and/or an absolute oral availability (F) of 10% or greater, more preferably 30% or greater.

The compounds according to the present invention are not antimetabolites, and show significantly lower toxic effects on cells compared with antimetabolites.

Preferably, the compounds according to the invention exhibit a high solubility in polar, protic solvents, such as in water (solubility (>10 μg/ml $H_2O$)) and/or their oral availability (F) is >30%. Moreover, preferably the compounds of the present invention are chemically stable and the manufacture thereof is inexpensive and straight forward. Accordingly, manufacture of the compounds of the present invention is cost effective.

Due to the mode of action of the compounds of the present invention, which involves the interaction with a host-cell based target, the generation of resistant viral strains is unlikely.

The following are examples of the compounds according to the present invention.

| Compound | Structure | IUPAC name |
|---|---|---|
| 1 | 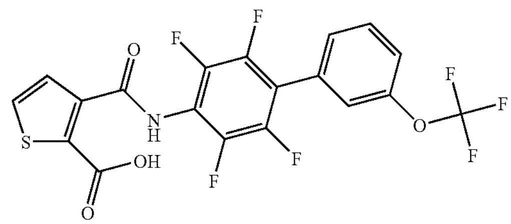 [SMILES: O=C(Nc1c(F)c(F)c(-c2cccc(OC(F)(F)F)c2)c(F)c1F)c1ccsc1C(=O)O] | 3-(2,3,5,6-Tetrafluoro-3'-trifluoromethoxy-biphenyl-4-ylcarbamoyl)-thiophene-2-carboxylic acid |
| 2 | 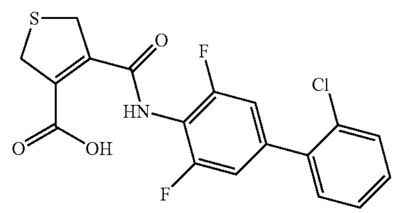 [SMILES: O=C(O)C1=C(C(=O)Nc2c(F)cc(-c3ccccc3Cl)cc2F)CSC1] | 4-(2'-Chloro-3,5-difluoro-biphenyl-4-ylcarbamoyl)-2,5-dihydro-thiophene-3-carboxylic acid |
| 3 | 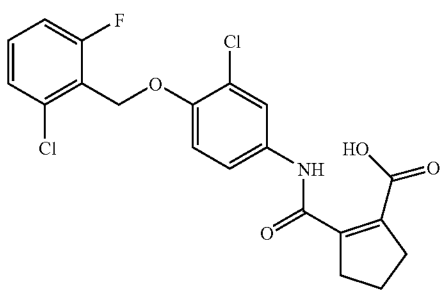 [SMILES: O=C(O)C1=C(C(=O)Nc2ccc(OCc3c(F)cccc3Cl)c(Cl)c2)CCC1] | 2-[3-Chloro-4-(2-chloro-6-fluoro-benzyloxy)-phenylcarbamoyl]-cyclopent-1-enecarboxylic acid |
| 4 | 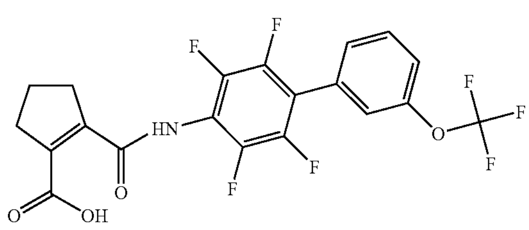 [SMILES: O=C(O)C1=C(C(=O)Nc2c(F)c(F)c(-c3cccc(OC(F)(F)F)c3)c(F)c2F)CCC1] | 2-(2,3,5,6-Tetrafluoro-3'-trifluoromethoxy-biphenyl-4-ylcarbamoyl)-cyclopent-1-enecarboxylic acid |
| 5 | 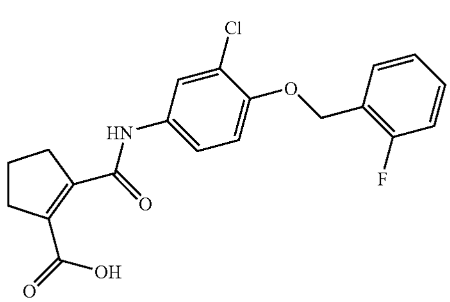 [SMILES: O=C(O)C1=C(C(=O)Nc2ccc(OCc3ccccc3F)c(Cl)c2)CCC1] | 2-[4-(2-Chloro-6-fluoro-benzyloxy)-3-fluoro-phenylcarbamoyl]-cyclopent-1-enecarboxylic acid |

-continued

| Compound | Structure | UPAC name |
|---|---|---|
| 6 | | 2-(3-Fluoro-3'-methoxy-biphenyl-4-ylcarbamoyl)-cyclopent-1-enecarboxylic acid |
| 7 | | 2-(3-biphenyl-4-ylureido)benzoic acid |
| 8 | | 2-(2,3,5,6-tetrafluoro-3'-methoxybiphenyl-4-ylcarbamoyl)furan-3-carboxylic acid |
| 9 | | 4-(3'-ethoxy-3,5-difluorobiphenyl-4-ylcarbamoyl)thiophene-3-carboxylic acid |
| 10 | | 2-(2,3,5,6-tetrafluoro-3'-methoxybiphenyl-4-ylcarbamoyl)cyclopent-1-enecarboxylic acid |
| 11 | | 2-(2,3,5,6-tetrafluoro-2'-methoxybiphenyl-4-ylcarbamoyl)cyclopent-1-enecarboxylic acid |

-continued

| Compound | Structure | UPAC name |
|---|---|---|
| 12 | | 2-(3,5-difluoro-3'-(trifluoromethoxy)biphenyl-4-ylcarbamoyl)cyclopent-1-enecarboxylic acid |
| 13 | | 3-hydroxy-2-(2,3,5,6-tetrafluoro-3'-(trifluoromethoxy)biphenyl-4-ylcarbamoyl)cyclopent-1-enecarboxylic acid |
| 14 | | 2-(2-chloro-4'-methoxybiphenyl-4-ylcarbamoyl)cyclopent-1-enecarboxylic acid |
| 15 | | 4-(3,5-difluoro-3'-(trifluoromethoxy)biphenyl-4-ylcarbamoyl)thiophene-3-carboxylic acid |
| 16 | | 5-(4-(2-chloro-6-fluorobenzyloxy)-3-fluorophenylcarbamoyl)cyclopenta-1,4-dienecarboxylic acid |
| 17 | | 3-(3,5-difluoro-3'-(trifluoromethoxy)biphenyl-4-ylcarbamoyl)thiophene-2-carboxylic acid |

| Compound | Structure | UPAC name |
|---|---|---|
| 18 | | 2-(3-fluoro-3'-methoxybiphenyl-4-ylamino)nicotinic acid |
| 19 | | 2-(3,5-difluoro-3'-methoxybiphenyl-4-ylamino)nicotinic acid |
| 20 | | 5-cyclopropyl-2-(5-methyl-6-(3-(trifluoromethoxy)phenyl)pyridin-3-ylamino)benzoic acid |
| 21 | | 2-[4-(2-Chloro-6-fluoro-benzyloxy)-3-fluoro-phenylcarbamoyl]-cyclopent-1-enecarboxylic acid |
| 22 | | 2-[3,5-Dichloro-4-(2-chloro-6-fluoro-benzyloxy)-phenylcarbamoyl]-cyclopent-1-enecarboxylic acid |
| 23 | | 2-(2-Chloro-4'-dimethylamino-biphenyl-4-ylcarbamoyl)-cyclopent-1-enecarboxylic acid |

-continued

| Compound | Structure | UPAC name |
|---|---|---|
| 24 | | 3-(3-Fluoro-3'-methoxy-biphenyl-4-ylcarbamoyl)-thiophene-2-carboxylic acid |
| 25 | | 4-(2,3,5,6-Tetrafluoro-3'trifluoromethoxy-biphenyl-4-ylcarbamoyl)-2,5-dihydro-thiophene-3-carboxylic acid |

The following are references used in the assays accomplished in the present invention:

| | | |
|---|---|---|
| Leflunomide metabolite A771726 | | (E)-2-cyano-3-hydroxy-N-(4-(trifluoromethyl)phenyl)but-2-enamide |
| Tipranavir | | N-(3-((R)-1-((S)-2-hydroxy-6-oxo-4-phenethyl-4-propylcyclohex-1-enyl)propyl)phenyl)-5-(trifluoromethyl)pyridine-2-sulfonamide |
| AZT | | 1-((2R,4S,5S)-4-azido-5-(hydroxymethyl)tetrahydrofuran-2-yl)-5-methylpyrimidine-2,4(1H,3H)-dione |

EXAMPLES

1. HIV (Human Immunodeficiency Virus)

Compounds according to the present invention were tested against human immunodeficiency virus 1 (HIV-1) in fresh human peripheral blood mononuclear cells (PBMCs). The antiviral activity and cytotoxicity against one CCR5-tropic HIV-1 isolate was tested.

1.1 Drug Preparation

Compounds were solubilized in DMSO in 40 mM concentration. The solubilized stocks were stored at −20° C. until the day of the assay. Stocks were thawed at room temperature on the day of the assay, and were used to generate working drug dilutions used in the assays. The compounds were evaluated using a 100 µM high-test concentration with 8 additional serial half-log dilutions in the PBMC assays (concentration range=100 µM to 0.01 µM). Azidothymidine (AZT) was included as a positive control antiviral compound in the assay.

1.2. Efficacy Evaluation in Human PBMCs a. Materials

Fresh human blood was obtained commercially from Biological Specialty Corporation (Colmar, Pa.). The clinical virus isolate HIV-1$_{91US005}$ (CCR5-tropic, Subtype B) was obtained from the NTH AIDS Research and Reference Reagent Program. A low passage stock of this virus was prepared using fresh human PBMCs and stored in liquid nitrogen. A pre-titered aliquot of this virus was removed from the freezer and thawed rapidly to room temperature in a biological safety cabinet immediately before use. Phytohemagglutinin (PHA) was obtained from Sigma (St. Louis, Mo.) and recombinant interleukin 2 (IL-2) was obtained from R&D Systems Inc. (Minneapolis, Minn.).

b. Anti-HIV Efficacy Evaluation in Fresh Human PBMCs

Fresh human PBMCs, seronegative for HIV and HBV, were isolated from screened donors. Cells were pelleted and washed 2-3 times by low speed centrifugation and re-suspension in PBS to remove contaminating platelets. The Leukophoresed blood was then diluted 1:1 with Dulbecco's Phosphate Buffered Saline (DPBS) (36 mg/L sodium pyruvate, 50 mg/L streptomycin sulfate, 100 mg/L kanamycin monosulfate, 1000 mg/L glucose, calcium chloride, and magnesium chloride) and layered over 14 mL of Lymphocyte Separation Medium (LSM; Cellgro® by Mediatech, Inc.; density 1.078+/−0.002 g/ml) in a 50 mL centrifuge tube and then centrifuged for 30 minutes at 600×g. Banded PBMCs were gently aspirated from the resulting interface and subsequently washed 2× with PBS by low speed centrifugation. After the final wash, cells were enumerated by trypan blue exclusion and re-suspended at 1×10$^6$ cells/mL in Roswell Park Memorial Institute medium 1640 (RPMI-1640) supplemented with 15% Fetal Bovine Serum (FBS), and 2 mM L-glutamine, 4 µg/mL Phytohemagglutinin (PHA, Sigma). The cells were allowed to incubate for 48-72 hours at 37° C. After incubation, PBMCs were centrifuged and resuspended in RPMI 1640 with 15% FBS, 2 mM L-glutamine, 100 U/mL penicillin, 100 ng/mL streptomycin, 10 µg/mL gentamycin, and 20 U/mL recombinant human IL-2 (R&D Systems, Inc). IL-2 is included in the culture medium to maintain the cell division initiated by the PHA mitogenic stimulation. PBMCs were maintained in this medium at a concentration of 1-2×10$^6$ cells/mL with medium changes twice a week until used in the assay protocol. Cells were kept in culture for a maximum of two weeks before being deemed too old for use in assays and discarded. Monocytes-derived-macrophages were depleted from the culture as the result of adherence to the tissue culture flask.

For the standard PBMC assay, PHA stimulated cells from at least two normal donors were pooled (mixed together), diluted in fresh medium to a final concentration of 1×10$^6$ cells/mL, and plated in the interior wells of a 96 well round bottom microplate at 50 µL/well (5×10$^4$ cells/well). Pooling (mixing) of mononuclear cells from more than one donor was used to minimize the variability observed between individual donors, which results from quantitative and qualitative differences in HIV infection and overall response to the PHA and IL-2 of primary lymphocyte populations. Each plate contains virus/cell control wells (cells plus virus), experimental wells (drug plus cells plus virus) and compound control wells (drug plus media without cells, necessary for MTS monitoring of cytotoxicity). In this in vitro assay, PBMC viability remains high throughout the duration of the incubation period. Therefore, infected wells were used in the assessment of both antiviral activity and cytotoxicity. Test drug dilutions were prepared at a 2× concentration in microliter tubes and 100 µL of each concentration was placed in appropriate wells using the standard format. 50 µL of a predetermined dilution of virus stock was placed in each test well (final MOI=0.1). The PBMC cultures were maintained for seven days following infection at 37° C., 5% CO$_2$ After this period, cell-free supernatant samples were collected for analysis of reverse transcriptase activity. Following removal of supernatant samples, compound cytotoxicity was measured by addition of MTS to the plates for determination of cell viability. Wells were also examined microscopically and any abnormalities were noted.

c. Reverse Transcriptase Activity Assay

A microtiter plate-based reverse transcriptase (RT) reaction was utilized (Buckheit et al., AIDS Research and Human Retroviruses 7:295-302, 1991). Tritiated thymidine triphosphate ($^3$H-TTP, 80 Ci/mmol, NEN) was received in 1:1 deionized H$_2$O:Ethanol at 1 mCi/mL. Poly rA:oligo dT template:primer (Pharmacia) was prepared as a stock solution by combining 150 µL polyriboadenylic acid (poly rA; 20 mg/mL) with 0.5 mL oligodeoxythymidylic acid (oligo dT; 20 units/mL) and 5.35 mL sterile deionized H$_2$O followed by aliquoting (1.0 mL) and storage at −20° C. The RT reaction buffer was prepared fresh on a daily basis and consisted of 125 µL 1.0 M ethylene glycol tetraacetic acid (EGTA), 125 µL deionized H$_2$O, 125 µL 20% Triton X100, 50 µL 1.0 M Tris (pH 7.4), 50 µL 1.0 M dithiothreitol (DTT), and 40 µL 1.0 M MgCl$_2$. The final reaction mixture was prepared by combining 1 part $^3$H-TTP, 4 parts deionized H$_2$O, 2.5 parts poly rA:oligo dT stock and 2.5 parts reaction buffer. Ten microliters of this reaction mixture was placed in a round bottom microtiter plate and 15 µL of virus containing supernatant was added and mixed. The plate was incubated at 37° C. for 60 minutes. Following incubation, the reaction volume was spotted onto DE81 filter-mats (Wallac), washed 5 times for 5 minutes each in a 5% sodium phosphate buffer or 2×SSC (Life Technologies). Next they were washed 2 times for 1 minute each in distilled water, 2 times for 1 minute each in 70% ethanol, and then dried. Incorporated radioactivity (counts per minute, CPM) was quantified using standard liquid scintillation techniques.

d. p24 Antigen ELISA

ELISA kits were purchased from XpressBio Life Science Products (Frederick, Md.). The assay was performed according to the manufacturer's instructions. Control curves were generated in each assay to accurately quantify the amount of p24 antigen in each sample. Data was obtained by spectrophotometric analysis at 450 nm using a Molecular Devices SpectraMaxPlus plate reader. Final p24 concentrations were calculated from the optical density values using the Molecular Devices SOFTmax Pro software package.

e. MTS Staining for MDM Viability to Measure Cytotoxicity

At assay termination, assay plates were stained with the soluble tetrazolium-based dye MTS (3-(4,5-Dimethylthiazol-2-yl)-5-(3-carboxymethoxyphenyl)-2-(4-sulfophenyl)-2H-tetrazolium; CellTiter 96 Reagent, Promega) to determine cell viability and quantify compound toxicity. At termination of the assay, 20 µL of MTS reagent was added per well. The microtiter plates were then incubated 4-6 hrs at 37° C. The incubation intervals were chosen based on empirically determined times for optimal dye reduction. Adhesive plate sealers were used in place of the lids, the sealed plate was inverted several times to mix the soluble formazan product formed and the plate was read spectrophotometrically at 490/650 nm with a Molecular Devices SpectraMaxPlus plate reader.

1.3. Data Analysis $IC_{50}$ (50% inhibition of virus replication), $IC_{90}$ (90% inhibition of virus replication), $IC_{50}$ (50% cytotoxicity), and therapeutic index values (TI=TC/IC; also referred to as Antiviral Index or AI) are calculated.

1.4. Results

A summary of the results from the experiments performed to determine the antiviral activity of compounds against HIV-$1_{91US005}$ in PBMC cultures is provided below in Table 1.

2. HCV (Hepatitis C Virus)

2.1. Compound Preparation

Compounds were solubilized in DMSO in a concentration of 40 mM. Recombinant human interferon alpha-2b (rIFNa-2b) was used as the positive antiviral controls. The high-test concentrations were 100 µM and 2 IU/mL for 4SC compounds and rIFNa-2b, respectively.

2.2. Cell Line Harboring the HCV Subgenomic Replicon

The ET cell line (luc-ubi-neo/ET) is a Huh7 human hepatoma cell line harboring an HCV subgenomic replicon of genotype 1b with a stable luciferase (Luc) reporter and three cell culture-adaptive mutations (Pietschmann, T., V. Lohmann, A. Kaul, N. Krieger, G. Rinck, G. Rutter, D. Strand, and R. Bartenschlager. 2002. Persistent and transient replication of full-length hepatitis C virus genomes in cell culture. J. Viral. 76:4008-4021) and was provided by Dr. Ralf Bartenschlager (Department of Molecular Virology, University of Heidelberg). The Luc reporter is used as an indirect measure replication of the HCV replicon since the activity of the Luc reporter is directly proportional to HCV RNA levels and positive control antiviral compounds behave comparably using either Luc or RNA endpoints.

The ET cell line was grown in Dulbecco's modified essential media (DMEM), 10% fetal bovine serum (FBS), 1% penicillin-streptomycin, 1% glutamine, 250 µg/ml Geneticin® (G418) in a 5% $CO_2$ incubator at 37° C. The assay medium for anti-HCV evaluation was DMEM with 5% fetal bovine serum (FBS), 1% penicillin-streptomycin and 1% glutamine.

2.3. Evaluation of Antiviral Activity Against the HCV Subgenomic Replicon

Compounds were evaluated in a modified HCV replicon assay. Brief description of the standard replicon assay: the ET cells were plated in 96-well plates (Costar) at $5 \times 10^4$ cells/well in DMEM with 10%, 1% penicillin-streptomycin and 1% glutamine. Two identical sets of plates were prepared which were dedicated to cytotoxicity or antiviral activity assessments each. On the following day, the test articles were diluted with the assay medium to make 6 half-log serial dilutions. Each of these dilutions was then applied to the corresponding wells of the ET cells. Human recombinant interferon alpha 1b (rIFNa-2b) was included as a positive control compound. After 24 h incubation, the cells were processed to derive, where applicable, $EC_{50}$ and $EC_{90}$ (concentrations resulting in 50% and 90% inhibitions, respectively), $IC_{50}$ (concentration decreasing cell viability by 50%) and $SI_{50}$ (selective index: $IC_{50}/EC_{50}$) values. HCV replicon levels

TABLE 1

Activity Against HIV-$1_{91US005}$ in Human PBMCs

| Compound | DHODH $IC_{50}$/nM | Endpoint | $EC_{50}$/nM | $EC_{90}$/nM | $TC_{50}$/nM | Therapeutic Index |
|---|---|---|---|---|---|---|
| 7 | +++ | RT | 50 | 210 | >100000 | >2046 |
|   |   | p24 | 60 | 230 |   | >1804 |
| 14 | ++ | RT | 5240 | 12200 | >100000 | >19 |
|   |   | p24 | 5180 | 16600 |   | >19 |
| 6 | ++ | RT | 2190 | 6110 | >100000 | >45 |
|   |   | p24 | 1970 | 6250 |   | >51 |
| 3 | +++ | RT | 190 | 700 | 44800 | 239 |
|   |   | p24 | 190 | 630 |   | 230 |
| 4 | +++ | RT | 60 | 210 | 42400 | 714 |
|   |   | p24 | 80 | 240 |   | 548 |
| 23 | ++ | RT | 1070 | 3480 | >100000 | >93 |
|   |   | p24 | 1000 | 3720 |   | >99 |
| 24 | ++ | RT | 3970 | 9070 | 55800 | 14 |
|   |   | p24 | 4540 | 12300 |   | 12 |
| 2 | +++ | RT | 920 | 2590 | >100000 | >109 |
|   |   | p24 | 1380 | 2770 |   | >72 |
| 1 | +++ | RT | 120 | 300 | >100000 | >842 |
|   |   | p24 | 170 | 300 |   | >598 |
| 25 | +++ | RT | 1560 | 3020 | >100000 | >64 |
|   |   | p24 | 1180 | 3160 |   | >85 |
| 8 | +++ | RT | 760 | 2700 | >100000 | >131 |
|   |   | p24 | 840 | 2970 |   | >119 |
| Leflunomide | + | RT | 6020 | 9410 | 95500 | 16 |
|   |   | p24 | 4940 | 9040 |   | 19 |
| Tipranavir | N.A. | RT | 60 | 150 | 67100 | 1188 |
|   |   | p24 | 60 | 250 |   | 1104 |

DHODH $IC_{50}$s: +++ = <20 nM; ++ = 20-200 nM; + = 200 nM – >1 µM; N.A, = not applicable were assessed with the replicon-derived Luc activity as readout. The cytotoxic concentrations of drug reducing cell numbers were assessed by the CytoTox-1 cell proliferation assay (Promega, Madison, Wis.) according to manufacturer's protocol. Modification of the standard protocol as applied to the substances in table 2: the compounds were tested with 6 half-log dilutions with high-test concentrations at 100 µM. The cells were at >75%© confluence when the compounds were applied and were processed 24 h after incubation with the test articles. In this assay, the positive control compound, human rIFNa-2b, was used in the replicon assay in parallel and yielded $IC_{50}$ values that fell within the acceptable ranges normally observed when performing antiviral assays.

2.4 Results

A summary of the results from the experiments performed to determine the antiviral activity of compounds against HCV in the replicon assay is provided below in Table 2.

TABLE 2

Activity in the modified HCV replicon assay

| Compound | DHODH $IC_{50}$/nM | Endpoint | Antiviral Activity $EC_{50}$/nM | $TC_{50}$/nM | Therapeutic Index |
|---|---|---|---|---|---|
| 6 | ++ | Replicon Luc | 4640 nM | >30 µM | >6 |
| 3 | +++ | Replicon Luc | 500 nM | >100 µM | >200 |
| 5 | ++ | Replicon Luc | 1790 nM | >30 µM | >16 |
| 21 | ++ | Replicon Luc | 1740 nM | >30 µM | >17 |
| 22 | ++ | Replicon Luc | 1760 nM | >30 µM | >17 |
| 4 | +++ | Replicon Luc | 80 nM | 83.77 µM | >1047 |
| 2 | +++ | Replicon Luc | 680 nM | >100 µM | >147 |
| 1 | +++ | Replicon Luc | 23 nM | >100 µM | >1250 |
| Leflunomide | ++ | Replicon Luc | >100 µM | >100 µM | 1 |
| rIFNa-2b | N.A. | Replicon Luc | 0.11 IU/mL | >2 IU/mL | >18.2 |

DHODH $IC_{50}$s: +++ = <20 nM; ++ = 20-200 nM; + = 200 nM – >1 µM; N.A. = not applicable 3. HBV (Hepatitis B Virus)

3.1. Compound Preparation

Compounds were solubilized in DMSO in a concentration of 40 mM. (−)-2'-Desoxy-3'-thiacytidin (3TC) was used as the positive antiviral controls. The high-test concentrations were 10 µM for 4SC compounds and 1 µM for 3TC.

3.2. Anti-HBV Evaluation with HepG2 2.2.15 Cells

Anti-HBV assay was performed as described in Korba, B F and Milman, G., 1991 (A cell culture assay for compound which inhibits hepatitis B virus replication. Antiviral Res. 15: 217-228) and in Korba, B F and Gerin, J L., 1992 (Use of a standardized cell culture assay to assess activities of nucleoside analogs again hepatitis B virus replication. Antiviral Res. 19: 55-70) with modifications to measure extracellular HBV DNA copy with real-time PCR (qPCR/TaqMan). Briefly, HepG2-2.2.15 cells were plated in 96-well microtiter plates. Only the interior wells were utilized to reduce "edge effects" observed during cell culture; the exterior wells were filled with complete medium to help minimize sample evaporation. After 16-24 hours the confluent monolayer of HepG2-2.2.15 cells was washed and the medium was replaced with complete medium containing various concentrations of a test compound in triplicate. 3TC was used as the positive control, while media alone was added to cells as a negative control. Three days later the culture medium was replaced with fresh medium containing the appropriately diluted drug. Six days following the initial administration of the test compound, the cell culture supernatant was collected, treated with pronase and then used in a quantitative qPCR TaqMan assay. Antiviral activity was calculated from the reduction in HBV DNA levels ($IC_{50}$). Cell Titer 96 ®AQueous One Solution Cell Proliferation kit (Promega, Madison, Wis.) was used to measure cell viability which is used to calculate toxicity ($TC_{50}$). The therapeutic index (TI) was calculated as $TC_{50}/IC_{50}$ 3.3. Results A summary of the results from the experiments performed to determine the antiviral activity of compounds against HBV is provided below in Table 3.

TABLE 3

Activity against HBV in HepG2 cells

| Compound | DHODH $IC_{50}$/nM | High-test concentration | Antiviral Activity $EC_{50}$ | $TC_{50}$ | Therapeutic Index |
|---|---|---|---|---|---|
| 3 | +++ | 10 µM | >10 µM | >10 µM | 1 |
| 4 | +++ | 10 µM | >10 µM | >10 µM | >1047 |
| 17 | +++ | 10 µM | 6.4 µM | >10 µM | >1.55 |
| 1 | +++ | 10 µM | 4.8 µM | >10 µM | >2.08 |
| 3TC | N.A. | 1 µM | 0.004 µM | >1 µM | >250 |

DHODH $IC_{50}$s: +++ = <20 nM; ++ = 20-200 nM; + = 200 nM – >1 µM; N.A. = not applicable 4. RSV (Respiratory Syncytial Virus), DENY (Dengue Virus), YFV (Yellow Fever Virus), WNV (West Nile Virus)

4.1. Compound Preparation

Compounds were solubilized in DMSO in a concentration of 40 mM. Ribavirin was used as the positive antiviral control. The high-test concentrations were 10 µM for 4SC compounds and 100 µg/mL (RSV, YFV, WNV) and 200 µg/mL (DENV) for Ribavirin.

4.2. Cytoprotection Antiviral Assays

A CPE (virus-induced cytopathic effects)-inhibition assay procedure was employed to evaluate compounds for antiviral activity against RSV (Long strain in Vero cells), Dengue virus (type 2 of strain New Guinea in Vero E6 cells), Yellow fever virus (D-17 strain in HeLa cells) and West Nile virus (NY-99 strain in Vero cells). The assay was performed as described in Buckwold, V. E., R. J. H. Wilson, A. Nalca, B. E. Beer, T. G. Voss, J. Turpin, R. W. Buckheit III, J. Wei, M. Wenzel-Mathers, E. M. Walton, R. J. Smith, M. Pallansch, P. Ward, J. Wells, L. Chuvala, S. Sloane, R. Paulman, J. Russell, T. Hartman, and R. Ptak. 2004. Antiviral activity of hop constituents against a series of DNA and RNA viruses. Antiviral Res. 61(1): 57-62. Antiviral assays were performed to evaluate 6 serial dilutions of each compound in triplicate against the challenge virus. Cell controls containing medium alone, virus infected cell controls containing medium and virus, compound cytotoxicity controls containing medium and each compound concentration, reagent controls containing culture medium only (no cells), and compound colorimetric controls containing compound and medium (no cells) were run simultaneously with the test samples. The plates were incubated at 37° C. in a humidified atmosphere containing 5% $CO_2$ until maximum CPE was observed in the untreated virus control cultures. CPE inhibition by the compound was determined by Cell Titer 96 ®Aqueous One Solution Cell Proliferation assay to derive the percent of CPE reduction of the virus infected wells and the percentage cell viability of uninfected compound control wells.

4.3. Results

A summary of the results from the experiments performed to determine the antiviral activity of compounds against RSV, DENV, YFV, and WNV is provided below in Tables 4, 5, 6, and 7, respectively.

TABLE 4

Activity against RSV Strain Long in Vero cells

| Compound | DHODH $IC_{50}$/nM | Hight-test concentration | Antiviral Activity $EC_{50}$ | $TC_{50}$ | Therapeutic Index |
|---|---|---|---|---|---|
| 3 | +++ | 10 μM | >10 μM | >10 μM | 1 |
| 4 | +++ | 10 μM | 2.15 μM | 7.96 μM | >3.70 |
| 17 | +++ | 10 μM | >10 μM | >10 μM | 1 |
| 1 | +++ | 10 μM | 2.1 μM | >10 μM | >4.88 |
| Ribavirin | N.A. | 100 μg/mL | 7.95 μg/mL | >100 μg/mL | >12.6 |

DHODH $IC_{50}$s: +++ = <20 nM; ++ = 20-200 nM; + = 200 nM – >1 μM; N.A. = not applicable

TABLE 5

Activity against DENV Type 2 (New Guinea) in Vero E6 cells

| Compound | DHODH $IC_{50}$/nM | Hight-test concentration | Antiviral Activity $EC_{50}$ | $TC_{50}$ | Therapeutic Index |
|---|---|---|---|---|---|
| 3 | +++ | 10 μM | 0.083 μM | 0.230 μM | 2.77 |
| 4 | +++ | 10 μM | 0.067 μM | 0.383 μM | 5.72 |
| 17 | +++ | 10 μM | >10 μM | 1.46 μM | <1.46 |
| 1 | +++ | 10 μM | 0.072 μM | 0.996 μM | 13.8 |
| Ribavirin | N.A. | 200 μg/mL | 26.5 μg/mL | >200 μg/μL | >7.55 |

DHODH $IC_{50}$s: +++ = <20 nM; ++ = 20-200 nM; + = 200 nM – >1 μM; N.A. = not applicable

TABLE 6

Activity against YFV Strain 17D in Vero cells

| Compound | DHODH $IC_{50}$/nM | Hight-test concentration | Antiviral Activity $EC_{50}$ | $TC_{50}$ | Therapeutic Index |
|---|---|---|---|---|---|
| 3 | +++ | 10 μM | 2.19 μM | >10 μM | >4.57 |
| 4 | +++ | 10 μM | 0.681 μM | 9.23 μM | 13.5 |
| 17 | +++ | 10 μM | 2.25 μM | >10 μM | >4.44 |
| 1 | +++ | 10 μM | 0.232 μM | >10 μM | >43.1 |
| Ribavirin | N.A. | 100 μg/mL | 7.33 μg/mL | >100 μg/mL | >13.6 |

DHODH $IC_{50}$s: +++ = <20 nM; ++ = 20-200 nM; + = 200 nM – >1 μM; N.A. = not applicable

TABLE 7

| | | Activity against WNV Strain NY-99 in Vero cells | | | |
|---|---|---|---|---|---|
| Compound | DHODH IC$_{50}$/nM | Hight-test concentration | Antiviral Activity EC$_{50}$ | TC$_{50}$ | Therapeutic Index |
| 3 | +++ | 10 μM | >10 μM | 0.237 μM | <0.237 |
| 4 | +++ | 10 μM | >10 μM | 0.206 μM | <0.206 |
| 17 | +++ | 10 μM | 6.39 μM | >10 μM | >1.56 |
| 1 | +++ | 10 μM | 0.735 μM | >10 μM | >13.6 |
| Ribavirin | N.A. | 100 μg/mL | 22.0 μg/mL | >100 μg/mL | >4.55 |

DHODH IC$_{50}$s: +++ = <20 nM; ++ = 20-200 nM; + = 200 nM – >1 μM; N.A. = not applicable

5. Influenza Virus
5.1. Inhibition of Influenza Virus Replication

A549 cells were infected with a highly pathogenic avian influenza virus strain (Fowl Plaque Virus, H7N7) for 16 hours (MOI=0.01). Cells were incubated with different concentrations of compounds or solvent (DMSO). The titer of next generation virus was determined in plaque assays. The virus number of the DMSO control was defined as 100%.

5.2. Results

A summary of the results from the experiments performed to determine the antiviral activity of compounds against influenza virus is provided below in Table 8.

TABLE 8

| | Activity against Influenza Virus (H7N7) | | | |
|---|---|---|---|---|
| Compound | DHODH IC$_{50}$/nM | Test concentration | Antiviral Activity % Inhibition | EC$_{50}$ |
| 4 | +++ | 30 μM | >90% | ca. 3 μM |
| 6 | ++ | 30 μM | >80% | |
| 9 | +++ | 30 μM | >80% | |
| 10 | +++ | 30 μM | >80% | |
| 11 | +++ | 30 μM | >90% | ca. 3 μM |
| 5 | ++ | 30 μM | >50% | |
| 12 | ++ | 30 μM | >80% | |
| 13 | +++ | 30 μM | >50% | |
| 8 | +++ | 30 μM | >50% | |
| 14 | ++ | 30 μM | >50% | |
| 15 | +++ | 30 μM | >80% | |

TABLE 8-continued

| | Activity against Influenza Virus (H7N7) | | | |
|---|---|---|---|---|
| Compound | DHODH IC$_{50}$/nM | Test concentration | Antiviral Activity % Inhibition | EC$_{50}$ |
| 1 | +++ | | | ca. 1.5 μM |
| 17 | +++ | | | ca. 3 μM |

DHODH IC$_{50}$s:
+++ = <20 nM;
++ = 20-200 nM;
+ = 200 nM->1 μM;
N.A. = not applicable

6. Ebola Virus
6.1. Inhibition of Ebola Virus Replication

Vero cells were inoculated with Ebola virus for 1 h. Then virus inoculums were removed and replaced with medium containing different concentrations of compounds or DMSO. After further incubation cell supernatants were removed and viral RNA titers determined. Also, the titers of infectious particles were determined with specific monoclonal antibodies. The virus number of the DMSO control was defined as 100%.

6.2. Results

A summary of the results from the experiments performed to determine the antiviral activity of compounds against Ebola virus is provided below in Table 9.

TABLE 9

| | Activity against Ebola Virus | | | | |
|---|---|---|---|---|---|
| Compound | DHODH IC$_{50}$/nM | Test concentration | Antiviral Activity % Inhibition | Test concentration | Antiviral Activity % Inhibition |
| 4 | +++ | 31.6 μM | >90% | 100 μM | >98% |
| 6 | ++ | 31.6 μM | 90% | 100 μM | >98% |

DHODH IC$_{50}$s: +++ = <20 nM; ++ = 20-200 nM; + = 200 nM – >1 μM; N.A. = not applicable 7. HCMV (Human Cytomegalovirus)
7.1. Inhibition of HCMV Replication Primary human foreskin fibroblasts are grown to a subcontinent cell layer (app. 90% confluency) and infected with HCMV AD 169-GFP at a GFP-delivering multiplicity of infection (GFP-MOI) of 0.25. (corresponding to 0.25% GFP-positive cells during the third round of infection at 7 days, i.e. 3 days per viral replication cycle). Virus adsorption is permitted for 1-2 h and thereafter virus is removed and cells are cultivated in fresh medium. Compounds are immediately added to the medium after the virus adsorption phase and HCMV-infected, substance-treated cells are incubated for 7 days at 37° C. GFP expression, HCMV-induced cytophathic effect, as well as putative drug-induced cytotoxicity of the substances were monitored.

7.2. Results

A summary of the results from the experiments performed to determine the antiviral activity of compounds against HCMV is provided below in Table 10.

TABLE 10

Activity against HCMV

| Compound | DHODH $IC_{50}$/nM | Hight-test concentration | Antiviral Activity $EC_{50}$ | $TC_{50}$ | Therapeutic Index |
|---|---|---|---|---|---|
| 1 | +++ | 10 µM | 0.780 µM | >10 µM | >12.8 |

DHODH $IC_{50}$s: +++ = <20 nM; ++ = 20-200 nM; + = 200 nM – >1 µM; N.A. = not applicable Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding European application No. 091593582, filed May 4, 2009, are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for the treatment or amelioration of a disease or medical condition caused by a viral infection, comprising administering to a subject in need thereof an effective amount of a dihydroorotate-dehydrogenase inhibitor of formula (I)

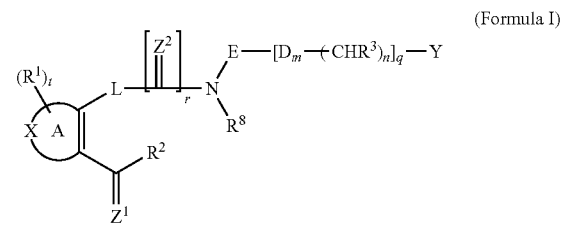

(Formula I)

wherein
A is furan, thiophene, phenyl, cyclopentenyl, cyclopentadienyl, pyridyl or dihydrothiophene;
L is a single bond;
D is O, or S;
$Z^1$ is O;
$Z^2$ is O;
R' independently represents H, —CO$_2$R", —CONR"R''', —CR"O, —SO$_2$NR", —NR"—CO-haloalkanyl, haloalkenyl, haloalkynyl, —NO$_2$, —NR"—SO$_2$-haloalkanyl, haloalkenyl, haloalkynyl, —NR"—SO$_2$-alkanyl, —NR"—SO$_2$-alkenyl, —NR"—SO$_2$-alkynyl, —SO$_2$-alkanyl, —SO$_2$-alkenyl, —SO$_2$-alkynyl, —NR"—CO-alkanyl, —NR"—CO-alkenyl, —NR"—CO-alkynyl, —CN, alkanyl, alkenyl, alkynyl, cycloalkyl, heterocycloalkyl, aminoalkanyl, aminoalkenyl, aminoalkynyl, alkanylamino, alkenylamino, alkynylamino, alkanyloxy, alkenyloxy, alkynyloxy, -cycloalkyloxy, —OH, —SH, alkanylthio, alkenylthio, alkynylthio, hydroxyalkanyl, hydroxyalkenyl, hydroxyalkynyl, hydroxyalkanylamino, hydroxyalkenylamino, hydroxyalkynylamino, halogen, haloalkanyl, haloalkenyl, haloalkynyl, haloalkanyloxy, haloalkenyloxy, haloalkynyloxy, aryl, aralkyl or heteroaryl;

R" independently represents hydrogen, haloalkanyl, haloalkenyl, haloalkynyl, hydroxyalkanyl, hydroxyalkenyl, hydroxyalkynyl, alkanyl, alkenyl, alkynyl, cycloalkyl, heterocycloalkyl, aryl, heteroaryl, aminoalkanyl, aminoalkenyl or aminoalkynyl;
R''' independently represents H or alkanyl;
$R^2$ is OR$^6$;
$R^3$ is H;
$R^6$ is H;
$R^8$ is hydrogen;
E is phenyl or pyridyl, each of which is optionally substituted by one or more substituents R';
Y is phenyl, which is optionally substituted by one or more substituents R';
m is 1;
n is 1;
q is 0 or 1;
r is 1; and
t is 0,
or a pharmacologically tolerable salt thereof,
or a physiologically functional derivative thereof, which is an ester, phosphate or sulfate modification of a hydroxyl group of a compound of formula I, an ester or amide modification of a carboxylic group of a compound of formula I, or an imine, amide or urea modification of an amino group of a compound of formula I,
wherein the viral infection is caused by a virus selected from the group consisting of Human Immunodefficiency Virus (HIV), Hepatitis C Virus (HCV), Hepatitis B Virus (HBV), Influenza, BK-Polyomavirus (BKV), Human Cytomegalo Virus (HCMV), Rift Valley Fever Virus (RVFV), Norovirus (NV), Lassa Virus (LV), Ebolavirus (EBOV), West Nile Virus (WNV), Dengue Virus (DV), Human Respiratory Syncytial Virus (RSV), and Yellow fever virus (YFV).

2. A method according to claim 1, wherein the viral infection is caused by Influenza.

3. A method according to claim 1, wherein the dihydroorotate-dehydrogenase inhibitor is a compound of formula (I) or a pharmacologically tolerable salt thereof.

4. A method according to claim 1, wherein transplant rejection is treated or ameliorated.

5. A method according to claim 3, wherein transplant rejection is treated or ameliorated.

6. A method according to claim 1, wherein transplant rejection is treated or ameliorated.

7. A method for the treatment or amelioration of a disease or medical condition caused by a viral infection,
comprising administering to a subject in need thereof an effective amount of one of the following dihydroorotate-dehydrogenase inhibitors:
3-(2,3,5,6-Tetrafluoro-3'-trifluoromethoxy-biphenyl-4-ylcarbamoyl)-thiophene-2-carboxylic acid;
4-(2'-Chloro-3,5-difluoro-biphenyl-4-ylcarbamoyl)-2,5-dihydro-thiophene-3-carboxylic acid;
2-[3-Chloro-4-(2-chloro-6-fluoro-benzyloxy)-phenylcarbamoyl]-cyclopent-1-enecarboxylic acid;
2-(2,3,5,6-Tetrafluoro-3'-trifluoromethoxy-biphenyl-4-ylcarbamoyl)-cyclopent-1-enecarboxylic acid;
2-[4-(2-Chloro-6-fluoro-benzyloxy)-3-fluoro-phenylcarbamoyl]-cyclopent-1-enecarboxylic acid;
2-(3-Fluoro-3'-methoxy-biphenyl-4-ylcarbamoyl)-cyclopent-1-enecarboxylic acid;
2-(3-biphenyl-4-ylureido)benzoic acid;
2-(2,3,5,6-tetrafluoro-3'-methoxybiphenyl-4-ylcarbamoyl)furan-3-carboxylic acid;
4-(3'-ethoxy-3,5-difluorobiphenyl-4-ylcarbamoyl)thiophene-3-carboxylic acid;
2-(2,3,5,6-tetrafluoro-3'-methoxybiphenyl-4-ylcarbamoyl)cyclopent-1-enecarboxylic acid;
2-(2,3,5,6-tetrafluoro-2'-methoxybiphenyl-4-ylcarbamoyl)cyclopent-1-enecarboxylic acid;
2-(3,5-difluoro-3'-(trifluoromethoxy)biphenyl-4-ylcarbamoyl)cyclopent-1-enecarboxylic acid;
3-hydroxy-2-(2,3,5,6-tetrafluoro-3'-(trifluoromethoxy)biphenyl-4-ylcarbamoyl)cyclopent-1-enecarboxylic acid;
2-(2-chloro-4'-methoxybiphenyl-4-ylcarbamoyl)cyclopent-1-enecarboxylic acid;
4-(3,5-difluoro-3'-(trifluoromethoxy)biphenyl-4-ylcarbamoyl)thiophene-3-carboxylic acid;
5-(4-(2-chloro-6-fluorobenzyloxy)-3-fluorophenylcarbamoyl)cyclopenta-1,4-dienecarboxylic acid;
3-(3,5-difluoro-3'-(trifluoromethoxy)biphenyl-4-ylcarbamoyl)thiophene-2-carboxylic acid;
2-(3-fluoro-3'-methoxybiphenyl-4-ylamino)nicotinic acid;
2-(3,5-difluoro-3'-methoxybiphenyl-4-ylamino)nicotinic acid;
5-cyclopropyl-2-(5-methyl-6-(3-(trifluoromethoxy)phenyl)pyridin-3-ylamino)benzoic acid;
2-[4-(2-Chloro-6-fluoro-benzyloxy)-3-fluoro-phenylcarbamoyl]-cyclopent-1-enecarboxylic acid;
2-[3,5-Dichloro-4-(2-chloro-6-fluoro-benzyloxy)-phenylcarbamoyl]-cyclopent-1-enecarboxylic acid;
2-(2-Chloro-4'-dimethylamino-biphenyl-4-ylcarbamoyl)-cyclopent-1-enecarboxylic acid;
3-(3-Fluoro-3'-methoxy-biphenyl-4-ylcarbamoyl)-thiophene-2-carboxylic acid; or
4-(2,3,5,6-Tetrafluoro-3'-trifluoromethoxy-biphenyl-4-ylcarbamoyl)-2,5-dihydro-thiophene-3-carboxylic acid;
or a pharmacologically tolerable salt thereof,
or a physiologically functional derivative thereof, which is an ester, phosphate or sulfate modification of a hydroxyl group of a compound of formula I, an ester or amide modification of a carboxylic group of a compound of formula I, or an imine, amide or urea modification of an amino group of a compound of formula I,
wherein the viral infection is caused by a virus selected from the group consisting of Human Immunodefficiency Virus (HIV), Hepatitis C Virus (HCV), Hepatitis B Virus (HBV), Influenza, BK-Polyomavirus (BKV), Human Cytomegalo Virus (HCMV), Rift Valley Fever Virus (RVFV), Norovirus (NV), Lassa Virus (LV), Ebolavirus (EBOV), West Nile Virus (WNV), Dengue Virus (DV), Human Respiratory Syncytial Virus (RSV), and Yellow fever virus (YFV).

8. A method according to claim 7, wherein transplant rejection is treated or ameliorated.

9. A method according to claim 7, wherein the dihydroorotate-dehydrogenase inhibitor is
3-(2,3,5,6-Tetrafluoro-3'-trifluoromethoxy-biphenyl-4-ylcarbamoyl)-thiophene-2-carboxylic acid;
4-(2'-Chloro-3,5-difluoro-biphenyl-4-ylcarbamoyl)-2,5-dihydro-thiophene-3-carboxylic acid;
2-[3-Chloro-4-(2-chloro-6-fluoro-benzyloxy)-phenylcarbamoyl]-cyclopent-1-enecarboxylic acid;
2-(2,3,5,6-Tetrafluoro-3'-trifluoromethoxy-biphenyl-4-ylcarbamoyl)-cyclopent-1-enecarboxylic acid;
2-[4-(2-Chloro-6-fluoro-benzyloxy)-3-fluoro-phenylcarbamoyl]-cyclopent-1-enecarboxylic acid;
2-(3-Fluoro-3'-methoxy-biphenyl-4-ylcarbamoyl)-cyclopent-1-enecarboxylic acid;
2-(3-biphenyl-4-ylureido)benzoic acid;
2-(2,3,5,6-tetrafluoro-3'-methoxybiphenyl-4-ylcarbamoyl)furan-3-carboxylic acid;
4-(3'-ethoxy-3,5-difluorobiphenyl-4-ylcarbamoyl)thiophene-3-carboxylic acid;
2-(2,3,5,6-tetrafluoro-3'-methoxybiphenyl-4-ylcarbamoyl)cyclopent-1-enecarboxylic acid;
2-(2,3,5,6-tetrafluoro-2'-methoxybiphenyl-4-ylcarbamoyl)cyclopent-1-enecarboxylic acid;
2-(3,5-difluoro-3'-(trifluoromethoxy)biphenyl-4-ylcarbamoyl)cyclopent-1-enecarboxylic acid;
3-hydroxy-2-(2,3,5,6-tetrafluoro-3'-(trifluoromethoxy)biphenyl-4-ylcarbamoyl)cyclopent-1-enecarboxylic acid;
2-(2-chloro-4'-methoxybiphenyl-4-ylcarbamoyl)cyclopent-1-enecarboxylic acid;
4-(3,5-difluoro-3'-(trifluoromethoxy)biphenyl-4-ylcarbamoyl)thiophene-3-carboxylic acid;
5-(4-(2-chloro-6-fluorobenzyloxy)-3-fluorophenylcarbamoyl)cyclopenta-1,4-dienecarboxylic acid;
3-(3,5-difluoro-3'-(trifluoromethoxy)biphenyl-4-ylcarbamoyl)thiophene-2-carboxylic acid;
2-(3-fluoro-3'-methoxybiphenyl-4-ylamino)nicotinic acid;
2-(3,5-difluoro-3'-methoxybiphenyl-4-ylamino)nicotinic acid;
5-cyclopropyl-2-(5-methyl-6-(3-(trifluoromethoxy)phenyl)pyridin-3-ylamino)benzoic acid;
2-[4-(2-Chloro-6-fluoro-benzyloxy)-3-fluoro-phenylcarbamoyl]-cyclopent-1-enecarboxylic acid;
2-[3,5-Dichloro-4-(2-chloro-6-fluoro-benzyloxy)-phenylcarbamoyl]-cyclopent-1-enecarboxylic acid;
2-(2-Chloro-4'-dimethylamino-biphenyl-4-ylcarbamoyl)-cyclopent-1-enecarboxylic acid;
3-(3-Fluoro-3'-methoxy-biphenyl-4-ylcarbamoyl)-thiophene-2-carboxylic acid; or
4-(2,3,5,6-Tetrafluoro-3'-trifluoromethoxy-biphenyl-4-ylcarbamoyl)-2,5-dihydro-thiophene-3-carboxylic acid;
or a pharmacologically tolerable salt thereof.

10. A method according to claim 9, wherein transplant rejection is treated or ameliorated.

11. A method according to claim 1, the viral infection is caused by BK-Polyomavirus (BKV).

12. A method according to claim 1, the viral infection is caused by Rift Valley Fever Virus (RVFV).

13. A method according to claim 1, the viral infection is caused by Norovirus (NV).

14. A method according to claim 1, the viral infection is caused by Lassa Virus (LV).

15. A method according to claim 1, the viral infection is caused by Ebolavirus (EBOV).

16. A method according to claim 1, the viral infection is caused by West Nile Virus (WNV).

17. A method according to claim 1, the viral infection is caused by Dengue Virus (DV).

18. A method according to claim 1, the viral infection is caused by Human Respiratory Syncytial Virus (RSV).

19. A method according to claim 1, the viral infection is caused by Yellow fever virus (YFV).

20. A method according to claim 7, wherein 3-(2.3.5.6-Tetrafluoro-3'-trifluoromethoxy-biphenyl-4-ylcarbamoyl)-thiophene-2-carboxylic acid or a pharmacologically tolerable salt thereof is administered.

21. A method according to claim 1, wherein
A is furan, thiophene, pyridyl or dihydrothiophene;
and wherein the dihydroorotate-dehydrogenase inhibitor has a half-maximal inhibitory concentration ($IC_{50}$) of 50 nM or less for the inhibition of dihydroorotate-dehydrogenase or less in an in vitro assay and a half-maximal effective concentration ($EC_{50}$) of 200 nM or less for inhibition of viruses in an in vitro assay.

22. A method according to claim 1, wherein
A is phenyl, cyclopentenyl or cyclopentadienyl;
and wherein the dihydroorotate-dehydrogenase inhibitor has a half-maximal inhibitory concentration ($IC_{50}$) of 50 nM or less for the inhibition of dihydroorotate-dehydrogenase or less in an in vitro assay and a half-maximal effective concentration ($EC_{50}$) of 200 nM or less for inhibition of viruses in an in vitro assay.

23. A method according to claim 1, wherein
A is furan, thiophene, pyridyl, or phenyl;
and wherein the dihydroorotate-dehydrogenase inhibitor has a solubility in water of 10 μg/mL or greater and/or an absolute oral availability (F) of 30% or greater.

24. A method according to claim 1, wherein
A is dihydrothiophene, cyclopentenyl or cyclopentadienyl;
and wherein the dihydroorotate-dehydrogenase inhibitor has a solubility in water of 10 μg/mL or greater and/or an absolute oral availability (F) of 30% or greater.

* * * * *